(12) United States Patent  
Kressner

(10) Patent No.: US 8,256,055 B2
(45) Date of Patent: Sep. 4, 2012

(54) TOOTHBRUSH

(75) Inventor: Gerhard Kressner, Altenstadt (DE)

(73) Assignee: Braun GmbH, Kronberg (DE)

( * ) Notice: Subject to any disclaimer, the term of this patent is extended or adjusted under 35 U.S.C. 154(b) by 155 days.

(21) Appl. No.: 12/663,757

(22) PCT Filed: Jun. 20, 2008

(86) PCT No.: PCT/EP2008/004978
§ 371 (c)(1),
(2), (4) Date: Dec. 9, 2009

(87) PCT Pub. No.: WO2009/000468
PCT Pub. Date: Dec. 31, 2008

(65) Prior Publication Data
US 2010/0170051 A1    Jul. 8, 2010

(30) Foreign Application Priority Data
Jun. 28, 2007  (DE) .......................... 10 2007 029 973

(51) Int. Cl.
*A61C 17/22*    (2006.01)

(52) U.S. Cl. ....................................... 15/22.1

(58) Field of Classification Search .............. 15/167.1, 15/22.1, 22.2, 23, 28, 29; *A61C 17/22*
See application file for complete search history.

(56) References Cited

U.S. PATENT DOCUMENTS

| | | |
|---|---|---|
| 1,420,388 A | 6/1922 | Schworm |
| 2,259,797 A | 10/1941 | Cohen |
| 2,911,660 A | 11/1959 | Klemas et al. |
| 3,034,376 A | 5/1962 | Gonzalez |
| 3,183,538 A | 5/1965 | Hibner |
| 3,195,537 A | 7/1965 | Blasi |
| 3,220,039 A | 11/1965 | Dayton et al. |
| 3,699,952 A * | 10/1972 | Waters et al. .................. 601/18 |
| 3,848,336 A | 11/1974 | Copeland |
| 3,851,984 A | 12/1974 | Crippa |

(Continued)

FOREIGN PATENT DOCUMENTS

CH    535 042 A    3/1973

(Continued)

OTHER PUBLICATIONS

PCT International Search Report dated Nov. 28, 2008.
PCT International Search Report dated Apr. 12, 2008.
Package rear and bottom panels of Bausch & Lomb Interplak Model PB-6, marked © 1992 (color copy, 1 sheet).

(Continued)

*Primary Examiner* — Mark Spisich
*Assistant Examiner* — Michael Jennings
(74) *Attorney, Agent, or Firm* — John P. Colbert

(57) ABSTRACT

The invention relates to an electric toothbrush. In one embodiment, the invention relates to the toothbrush handle part having a coupling device for coupling an attachment thereto, especially an attachable brush, and a drive train, especially a drive shaft, which can be driven by a drive motor, for driving the attachment. In another embodiment, the invention relates to the above attachment which especially may be an attachable brush, comprising a connecting piece that can be placed on the handle part neck of the toothbrush handle part. The toothbrush handle part comprises disengageable arresting means for arresting, blocking, and/or braking the drive train part. Advantageously, the arresting means are automatically released when the attachable brush is attached and are transferred to the arrested state when the attachable brush is removed. In the arrested state of the drive train part, the drive motor is automatically switched off.

9 Claims, 21 Drawing Sheets

U.S. PATENT DOCUMENTS

Figure 1:
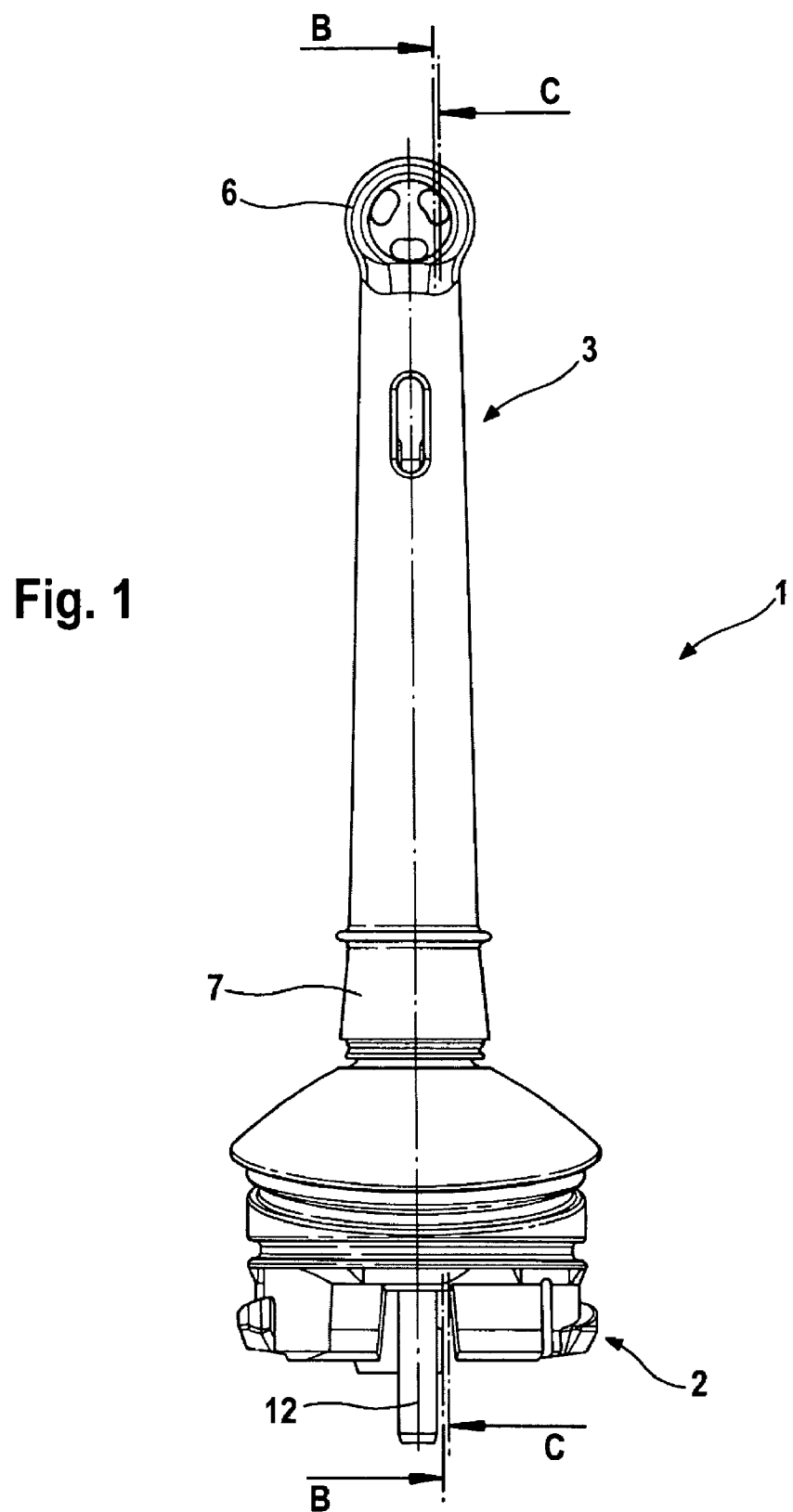

| | | | |
|---|---|---|---|
| 3,927,435 A | 12/1975 | Moret et al. | |
| 3,939,599 A | 2/1976 | Henry et al. | |
| 4,156,620 A | 5/1979 | Clemens | |
| 4,365,376 A * | 12/1982 | Oda et al. | 15/22.1 |
| 4,391,547 A | 7/1983 | Jackson, Jr. | |
| 4,811,445 A | 3/1989 | Lagieski et al. | |
| 4,827,550 A | 5/1989 | Graham et al. | |
| 4,827,552 A | 5/1989 | Bojar et al. | |
| 4,989,287 A | 2/1991 | Scherer | |
| 5,054,149 A | 10/1991 | Si-Hoe et al. | |
| 5,213,434 A | 5/1993 | Hahn | |
| 5,289,604 A | 3/1994 | Kressner | |
| 5,337,435 A | 8/1994 | Krasner et al. | |
| 5,359,747 A | 11/1994 | Amakasu | |
| 5,365,627 A | 11/1994 | Jousson et al. | |
| 5,435,032 A | 7/1995 | McDougall | |
| 5,461,744 A | 10/1995 | Merbach | |
| 5,561,881 A | 10/1996 | Klinger et al. | |
| 5,625,916 A | 5/1997 | McDougall | |
| 5,812,065 A | 9/1998 | Schrott et al. | |
| 5,943,723 A | 8/1999 | Hilfinger et al. | |
| 6,177,870 B1 | 1/2001 | Lian et al. | |
| 6,308,359 B2 | 10/2001 | Fritsch et al. | |
| 6,359,559 B1 | 3/2002 | Rudell et al. | |
| 6,367,108 B1 | 4/2002 | Fritsch et al. | |
| 6,545,576 B1 | 4/2003 | Marchini et al. | |
| 6,581,234 B2 * | 6/2003 | Lee et al. | 15/28 |
| 6,588,042 B2 | 7/2003 | Fritsch et al. | |
| 6,590,763 B2 | 7/2003 | Kishimoto | |
| 6,636,135 B1 | 10/2003 | Vetter | |
| 6,734,795 B2 | 5/2004 | Price | |
| 6,750,747 B2 | 6/2004 | Mandell et al. | |
| 6,766,548 B1 | 7/2004 | Lukas et al. | |
| 6,792,640 B2 | 9/2004 | Lev | |
| 6,836,917 B2 | 1/2005 | Blaustein et al. | |
| 6,868,919 B1 | 3/2005 | Manschitz et al. | |
| 6,952,855 B2 | 10/2005 | Lev et al. | |
| 6,954,961 B2 | 10/2005 | Ferber et al. | |
| 7,024,717 B2 | 4/2006 | Hilscher et al. | |
| 7,086,111 B2 | 8/2006 | Hilscher et al. | |
| 7,207,080 B2 | 4/2007 | Hilscher et al. | |
| 7,422,582 B2 | 9/2008 | Malackowski et al. | |
| 7,431,682 B2 | 10/2008 | Zeiler et al. | |
| 7,443,058 B2 * | 10/2008 | Shimizu et al. | 310/12.04 |
| 7,562,121 B2 | 7/2009 | Berisford et al. | |
| 7,621,015 B2 | 11/2009 | Hilscher | |
| 7,624,467 B2 | 12/2009 | Hilscher et al. | |
| 7,770,251 B2 * | 8/2010 | Hilscher et al. | 15/22.1 |
| 7,845,039 B2 | 12/2010 | Chan et al. | |
| 7,887,559 B2 | 2/2011 | Deng et al. | |
| 7,979,939 B2 | 7/2011 | Hilscher | |
| 2002/0196113 A1 | 12/2002 | Rudd et al. | |
| 2003/0101526 A1 | 6/2003 | Hilscher et al. | |
| 2003/0135940 A1 | 7/2003 | Lev et al. | |
| 2004/0255409 A1 | 12/2004 | Hilscher et al. | |
| 2005/0000044 A1 | 1/2005 | Hilscher | |
| 2005/0271531 A1 | 12/2005 | Brown, Jr. et al. | |
| 2005/0272001 A1 | 12/2005 | Blain et al. | |
| 2005/0272002 A1 | 12/2005 | Chenvainu et al. | |
| 2006/0048797 A1 | 3/2006 | Jung et al. | |
| 2006/0145871 A1 | 7/2006 | Donati et al. | |
| 2007/0234493 A1 | 10/2007 | Hilscher | |
| 2010/0043156 A1 | 2/2010 | Kressner | |
| 2010/0101032 A1 | 4/2010 | Kressner | |
| 2010/0162498 A1 | 7/2010 | Kressner | |
| 2010/0170051 A1 | 7/2010 | Kressner | |

FOREIGN PATENT DOCUMENTS

| | | |
|---|---|---|
| DE | 24 30 921 | 1/1976 |
| DE | 35 10 909 | 7/1987 |
| DE | 39 36 714 | 5/1991 |
| DE | 40 12 413 | 10/1991 |
| DE | 38 80 015 | 9/1993 |
| DE | 42 34 764 | 4/1994 |
| DE | 195 06 129 | 8/1996 |
| DE | 195 08 932 | 9/1996 |
| DE | 196 28 574 | 3/1997 |
| DE | 195 45324 | 6/1997 |
| DE | 297 02 508 | 5/1998 |
| DE | 197 17 334 | 7/1998 |
| DE | 197 45 876 | 4/1999 |
| DE | 100 01 502 | 3/2001 |
| DE | 100 26 513 | 5/2001 |
| DE | 101 35 257 | 2/2002 |
| DE | 10045 353 | 3/2002 |
| DE | 100 45 067 | 4/2002 |
| DE | 101 01 163 | 7/2002 |
| DE | 101 12 601 A1 | 9/2002 |
| DE | 101 59 395 A1 | 6/2003 |
| DE | 103 52 993 | 6/2005 |
| EP | 0300345 | 1/1989 |
| EP | 0435329 | 7/1991 |
| EP | 0 500 537 | 11/1994 |
| EP | 1267664 | 6/2004 |
| EP | 1 256 327 | 12/2005 |
| EP | 1244373 | 7/2006 |
| FR | 2832298 | 5/2003 |
| WO | WO 00/76420 | 12/2000 |
| WO | WO 02071970 | 9/2002 |

OTHER PUBLICATIONS

Color photographs of Bausch & Lomb "Interplak" Model PB-6 style Handpiece with waterproof electronic travel protection switch (believed circa 1992 on sale in the United States) (6 views).

Product use instructions to Bausch & Lomb Interplak travel-style "Voyager" model TK-2 marked © 1991 (6 photocopies sheets containing cover and pp. 1-10).

Color photographs of Bausch & Lomb "Interplak" Model PB-4B style Handpiece with travel protection switch and Toothbrush attachment (handpiece stamped "1D IA", believed circa 1992 on sale in the United States) (2 sheets with 7 views).

Package rear and bottom panels of Bausch & Lomb Interplak Model PB-4B, marked © 1990 (color copy, 1 sheet).

"RFID Made Easy" Handbook by EM Microelectronic—Marin SA, 2074 Marin, Switzerland, copr 2000 and dated Mar. 2001,, Rev. C/350, pp. 1-33.

Finkenzeller, Laus, "RFID-Handbuch, Grundlagen und praktische Anwendungen induktiver Funkanlagen, Transponder und kontaktloser Chipkarten" [Trans: "RFID Handbook. Fundamentals and Practical Applications to Inductive Radio Communications, Transponders and Contactless Chip Cards"], Carl Hanser Verlag Munchen, $2^{nd}$ Edtiion, Chapter 3, pp. 29-58 w/title page and Impressum. Contents pp. vii-xviii, and Appendices 15.2 "Standards" and 15.3 "Literature" on pp. 393-406.

Herzer, Gieselher, "Der grosse Lauschangriff auf Ladendiebe" [transl. "The great surveillance of shoplifters"] in Physikalische Blaetter [transl: Physics Letters] vol. 57, (2001), No. 5, pp. 43-48.

Office Action from U.S. Appl. No. 11/257,603, dated Sep. 20, 2006.
Office Action from U.S. Appl. No. 11/257,603, dated Nov. 25, 2008.
Office Action from U.S. Appl. No. 11,763,338, dated Jul. 10, 2008.
Office Action from U.S. Appl. No. 11/888,212, dated Mar. 21, 2008.
Office Action from U.S. Appl. No. 11/888,250, dated Jun. 3, 2008.
Office Action from U.S. Appl. No. 11/888,251, dated Mar. 21, 2008.
Office Action from U.S. Appl. No. 11/763,338, dated Dec. 4, 2008.
Office Action from U.S. Appl. No. 10/872,016, dated Apr. 10, 2009.
Office Action from U.S. Appl. No. 10/872,075, dated Jun. 4, 2009.
Office Action from U.S. Appl. No. 11/763,338, dated Mar. 24, 2009.
Office Action from U.S. Appl. No. 11/888,212, dated Mar. 17, 2009.
Office Action from U.S. Appl. No. 11/888,251, dated Mar. 17, 2009.
Office Action from U.S. Appl. No. 11/888,386, dated Mar. 3, 2009.
Office Action from U.S. Appl. No. 11/890,083, dated Mar. 16, 2009.
PCT Search Report PCT/EP 01/02844, dated Aug. 8, 2001 for U.S. Appl. No. 10/662,237.
PCT Search Report PCT/EP 01/028262, dated Jul. 31, 2001 for U.S. Appl. No. 09/811,080.
PCT Search Report PCT/EP 02/01724, dated Jul. 17, 2002 for U.S. Appl. No. 10/241,274.
Office Action from U.S. Appl. No. 12/627,367, dated Sep. 15, 2010.

* cited by examiner

TOOTHBRUSH

The present invention relates to an electric toothbrush. On the one hand, the present invention relates to a toothbrush handle having a coupling device for coupling an attachment part, in particular a brush attachment, as well as a drive train part capable of being driven by a drive motor, in particular a drive shaft, to drive the attachment part. On the other hand, the present invention relates to the named attachment part, which in particular can form a brush attachment, having a connecting piece that is capable of being attached onto the handle neck of the toothbrush handle.

From EP 0 500 537 B1, an electric toothbrush is known in which the brush attachment is connected on the one hand to a shaft-shaped handle neck of the toothbrush handle that protrudes at a front end, and on the other hand is connected to a drive shaft protruding therefrom. Here, the handle neck is formed approximately in the shape of a cylindrical stub, so that the approximately tube-shaped connecting piece of the brush attachment can be attached onto the handle neck so as to grip it with a precise fit.

In such attachable brush attachments, the vibrations of the toothbrush drive and brushing forces sometimes cause an undesired disengagement of the fastening of the attachment part, whereby the transmission of the drive movement to the brush attachment is impaired and the drive train is subjected to increased wear; if the attachment part slides all the way off, there is even a risk of injury from the drive shaft protruding from the frontal end. In order to prevent this, up to now the fit between the handle neck and the brush attachment has often been chosen to be so tight that the brush attachment can be attached onto or removed from the handle neck only with a large exertion of force. To the extent that, in contrast, snap-on connection means have been provided between the brush attachment and the toothbrush handle; the tolerances required for simple snapping on often impair the freedom of play and precision of fit of the connection. In addition, the cited problem of wear in the drive train and of the risk of injury exists if the connection between the plug-on brush and the toothbrush handle should nonetheless become disengaged.

On the other hand, such electric toothbrushes have also exhibited the problem that they sometimes turn on in undesired fashion. In particular when transported in a tightly packed suitcase on trips, the pressure acting on the switch from the surrounding objects can cause unwanted turning on of the motor. It is true that lockable switch-on buttons are known, which can for example be fixed in the off position by means of a slidable lock. However, this lock can itself be unlocked by the pressure in a suitcase, so that switching on may occur. This can result in undesirable discharge of the battery, but also in damage to the brush or to the surrounding objects if the brush head or the protruding shaft of the brush attachment has been removed and rubs against the objects.

Against this background, the present invention is based on the object of creating an improved toothbrush, an improved toothbrush handle, and/or an improved attachment part for such a toothbrush handle, which avoid the disadvantages of the prior art and develop the prior art in an advantageous manner. Preferably, a connection between the attachment part and the toothbrush handle is to be created that is easily operated with small forces, and that provides the attachment part with a secure hold on the toothbrush handle, prevents unwanted activation of the toothbrush drive train, and removes any risk of injury from the drive train of the toothbrush handle.

Thus, it is proposed that a drive train part, in particular the drive shaft of the toothbrush handle, can be blocked or arrested, so that no dangerous movement of the drive train can occur even in the case of unwanted switching on of the drive motor. The toothbrush handle has disengageable arresting means for the arresting, blocking, and/or braking of the drive train part.

Advantageously, the arresting means are designed in such a way that they are actuated automatically when the attachment part is placed onto or removed from the toothbrush handle, in particular in such a way that when a brush attachment is placed on the handle the arresting means are released, and when the brush attachment is removed the arresting means are brought into their arresting state.

Advantageously, the named arresting means can work together with an electronic switch-off mechanism for the drive motor. In particular, a preferably electronic switch-off device can be provided that switches off the drive motor when there is arresting of the drive shaft. As soon as the electronic switch-off device registers that the drive shaft of the toothbrush cannot move freely, a switching off of the drive motor takes place in order to protect the motor and in particular also the batteries. The detection of the arresting situation of the drive shaft can in principle take place in various ways. For example, a position sensor could be provided that detects the position of the aforementioned arresting piece. When this arresting piece is in its arresting position, the drive motor is switched off. In an advantageous embodiment, the switching off of the motor can however also take place on the basis of its power consumption. In particular, the aforementioned switch-off device can comprise means for detecting the motor current, and can switch off the drive motor when the motor current exceeds a predetermined level. This occurs when the drive shaft is blocked or arrested. In order to avoid unwanted switching off during brief current or voltage peaks, the switch-off device can be designed such that the motor does not switch off until the motor current remains above the predetermined threshold value for more than a predetermined length of time, for example longer than 5 seconds.

Through such mechanical arresting of the drive shaft of the toothbrush handle when the attachment part is removed, in connection with an electronic switching off of the drive motor, a very simple travel safety system with battery protection can be achieved. The attachment part need merely be removed from the toothbrush handle in order to prevent unwanted switching-on of the toothbrush handle. Even if this handle is for example placed loosely into a suitcase, the battery of the toothbrush cannot discharge unintentionally.

In order to achieve an automatic actuation of the arresting means when the attachment part is attached and removed from the handle, a control device is allocated to the arresting means which controls the engagement position of the arresting means as a function of the position of the coupling device, wherein the control device advantageously is designed such that the arresting means is released when the attachment part is connected, and is in its arresting position when the attachment part is removed. This can prevent the toothbrush drive from moving if the brush attachment is not correctly seated on the handle, so that in particular a risk of injury due to a rotating drive shaft can be prevented. The named arresting means can be designed in various ways, wherein, in principle, it would be conceivable to design the arresting means in terms of control technology or software. Alternatively, or in addition, a mechanical construction of the arresting means may be provided, wherein in this case, the arresting means can advantageously comprise an engagement surface on the arresting piece that, in the non-locking position of the arresting piece, can move into engagement with a drive shaft of the handle, and in particular can be pressed onto the drive shaft. In particular, the arresting means can comprise flat areas on the drive shaft and on the named arresting piece on the handle that can be moved onto one another. In order to achieve a better hold in the arresting position, the flat areas can also be made complementary, concave and convex, for example slightly V-shaped and, complementary thereto, with a slight bulge. When the arresting piece presses with its flat area on a corresponding flat area of the drive shaft, the latter can no longer rotate. The named flat areas are advantageously situated on the jacket surface. The control device for actuating the arresting means as a function of the coupling state of the attachment part can in principle be realized in various ways.

Advantageously, on its handle neck the handle can have an arresting piece having at least one engagement part that can be brought into engagement with the drive shaft in order to bring about a positive and/or frictional locking, arresting, or braking, wherein the arresting piece is advantageously capable of movement in the longitudinal direction of the handle. The arresting piece is preferably pressed axially away from the grip part of the toothbrush handle by a spring element, so that when the brush attachment is not placed on the handle, the arresting piece is situated in a defined position relative to the handle, in which the attachment part can be attached without hindrance and the drive shaft is blocked or arrested. Preferably, the handle neck is designed in one piece with the housing of the handle.

The arresting means on the handle neck preferably operate with an axial movement in the longitudinal direction of the handle, as well as a transverse movement transverse to the longitudinal direction of the handle, wherein the axial movement in the longitudinal direction of the handle advantageously effects the actuation of the arresting means and the transverse movement advantageously effects the locking. Advantageously, the toothbrush handle has an arresting piece that is capable of axial movement in the longitudinal direction of the handle, said arresting piece is mounted and/or designed in such a way that an axial movement of the arresting piece produces a transverse movement of the engagement part of the arresting means transverse to the longitudinal direction of the handle.

Here, the axial actuation movement can advantageously be produced by the attachment part when it is attached to or removed from the handle neck. The attaching or removing of the attachment part can, so to speak, be used to produce a locking or unlocking movement, oriented transversely to the attaching or removing movement, of the arresting means on the handle. According to a further aspect, the attachment part is characterized in that its connecting piece, which is capable of being connected to the handle, has an abutting surface for the axial pushing back of the arresting piece on the handle during the placement of the connecting piece onto the handle neck. The named abutting surface on the attachment part is advantageously matched in its shape and position to the arresting piece on the handle in such a way that the abutting surface catches the arresting piece of the toothbrush handle when the attachment part and the toothbrush handle are placed together and slides the arresting piece back axially towards the grip of the toothbrush handle, so that the locking is, so to speak, automatically brought about when the attachment part is attached.

In order to bring about the transverse movement of the engagement part of the arresting means that produces the locking, a spreading mechanism is preferably provided between the handle neck and the arresting piece of the toothbrush handle, by which the aforementioned engagement part is pressed or drawn inward, away from the grip part, transverse to the longitudinal direction of the handle, upon axial movement of the named arresting piece. Advantageously, the arresting piece itself is spread inward by the named spreading mechanism when there is corresponding axial movement, so that the named engagement part can be provided immediately on the arresting piece, preferably integrally formed thereon in one piece.

Here, the named spreading mechanism can in principle be designed in various ways. For example, the transverse movement can be brought about by a pair of oblique surfaces. For example, the arresting piece can run onto an oblique surface provided on the handle neck, so that the arresting piece is pressed inward when it is slid back away from the grip part.

The spreading mechanism is preferably designed as a compulsory guide that prevents a transverse movement of the arresting piece without axial movement of the arresting piece, and/or vice versa. The spreading mechanism is therefore designed in such a way that not only an outward movement of the arresting piece is ensured when there is a corresponding axial movement, but an inward movement is also ensured when there is an opposed axial movement.

The arresting piece can be mounted on the handle neck by a rod guide having at least one connecting rod that, in an advantageous embodiment, is connected pivotably to the handle neck at one end and is connected pivotably at its other end to the arresting piece, wherein the pivot axes advantageously is oriented transverse to the longitudinal direction of the handle.

In principle, it can be sufficient to link the arresting piece to only one rod in the area of the engagement part in order to achieve the desired spreading in the area of the engagement part. Here, the arresting piece could be guided in longitudinally displaceable fashion on the handle neck, on a segment situated at a distance from the engagement part, so that an overall two-impact-type construction would result. Preferably, however, the arresting piece is linked by a parallelogram rod guide to at least two rods on the handle neck that are oriented approximately parallel to one another, so that the arresting piece can be displaced on a movement path, predetermined by the rods, in parallel fashion, essentially without a rotational component. Here, the parallelogram rod guide is constructed in such a way that when there is an axial movement of the arresting piece in the longitudinal direction of the handle, a cross-movement component, transverse thereto, is produced.

Alternative to such a pivot rod guide, the arresting piece can also be spread by means of a sliding guide, wherein the arresting piece advantageously is guided in compulsory fashion by the sliding guide in such a way that an axial movement of the arresting piece is compulsorily converted into a radial movement. Advantageously, the compulsory guiding is given in both directions; i.e., when the arresting piece moves in the one direction the arresting piece is pressed outward, whereas it is pressed inward when the movement is in the opposite direction.

Here, the sliding guide can, for example, be designed in the form of a channel guide, preferably a dovetail channel guide, which advantageously guides the arresting piece in sliding fashion on opposite sides.

The named sliding guide can advantageously be designed as a sliding block guide that preferably has a guide slotted link in the arresting piece as well as at least one guide nose that engages therein on the handle neck. Here, the arresting piece forms, so to speak, a sliding block that can be spread along a predetermined path via the sliding block guide. Alternatively, or in addition, a guide slotted link can be provided on the handle neck in which the arresting piece engages with a guide projection.

The magnitude and distance of the spreading movement can be controlled through the incline of the sliding block guide. Advantageously, here the sliding block guide comprises a plurality of guide segments having different inclinations, so that different spreading movements take place depending on the axial position of the arresting piece. In particular, the sliding block guide can comprise beginning and end segments having only a slight inclination, or advantageously running parallel to the longitudinal direction of the handle, essentially without an inclination, between which a center guide segment having a larger inclination is provided. In this way, it can be achieved that in the end segments the only slightly inclined, or uninclined, guide segments can hold the arresting piece in the respective position essentially without axial forces. In contrast, the desired spreading movement can be achieved via the more strongly inclined center guide segment. When this is achieved, the slide block guide travels, so to speak, on a plateau by means of which the respective position is held. Optionally, the named beginning and end segments can be inclined slightly in opposite directions to the named center segment, so that during movement into the end position, so to speak, a slight excess pressure of the arresting piece takes place, and the arresting piece remains securely in the respective end position.

Alternative to an arresting piece that is movable in a sliding guide, a pivotably mounted arresting piece can also be provided that combines an axial actuating movement component with a transverse movement component via a rotational movement. In particular, the arresting piece can be designed as a pivotably mounted cam that is mounted on the handle neck so as to be pivotable about a pivot axis that preferably runs transverse to the longitudinal direction of the toothbrush. The named cam is brought into engagement with the drive shaft by rotating it into its arresting position, whereas it releases the named drive shaft when rotated in the opposite direction.

Advantageously, the arresting means simultaneously form a coupling device for the positive and/or frictional locking of the attachment part on the handle neck. This double function can advantageously be achieved in that the arresting piece simultaneously forms a coupling piece that can be brought into engagement with the connecting piece of the attachment part on the handle neck through movement in the longitudinal direction of the handle and transverse thereto. In particular, the position of the arresting piece in which it is disengaged from the drive shaft can simultaneously form the locking position of the coupling piece, i.e., the arresting piece locks the attachment part while in its disengaged position from the drive shaft.

Here, the arresting piece can have, in particular on its radially outwardly situated side, an engagement part, for example in the form of an engagement protuberance that can be moved into an outwardly oriented recess that is provided on an inner jacket surface of the connecting piece or of a coupling piece, set therein, of the attachment part. Alternatively, or in addition, a resilient snap connection can also be provided between the arresting piece and the attachment part. Furthermore, alternatively or in addition, a frictional locking can be provided between the arresting piece and the attachment part, for example in that the outer side of the arresting piece is pressed against the inner jacket surface of the attachment part.

In order to enable the axial movement of attaching the attachment part onto the handle neck to be used for the actuation of the arresting means, a catch segment is provided on the arresting piece on the handle that catches an abutting surface provided on the connecting piece of the attachment part when the attachment part is attached onto the handle neck, so that the abutting surface moves the catch segment, and therewith the arresting piece, axially onto the grip part of the toothbrush handle when the attachment part is pressed onto the handle neck. In particular, a pair of abutting surfaces can be provided on the arresting piece on the handle and on the connecting piece of the attachment part that extends transverse to the longitudinal direction of the handle or the longitudinal direction of the attachment part, wherein the members of said pair are matched to one another with regard to their position and orientation in such a way that when the attachment part is placed onto the handle neck, the abutting surfaces are compelled to move into engagement, and bring about the desired axial displacement of the arresting piece on the handle. Advantageously, here the abutting surfaces that catch one another are constructed in such a way that not only is the axial actuation for the arresting piece on the handle removed, but also the transverse movement thereby provided from the arresting piece on the handle is possible. In particular, the arresting piece on the handle, or its abutting surface, can slide transverse to the longitudinal direction of the handle on the abutting surface on the attachment part. The segments on the handle and on the attachment part that catch one another and that bring about the axial actuation of the arresting piece thus form, so to speak, a pair of gliding surfaces that slide on one another when the attachment part is axially pushed on.

In order, conversely, to bring about an automatic disengagement of the arresting piece when the attachment part is removed from the toothbrush handle, and to drive the arresting piece axially, an driving surface pair is provided on the attachment part and on the arresting part on the handle that preferably extends transverse to the axial direction and that forms, in the manner named above, a pair of gliding surfaces in order to permit sliding transverse to the longitudinal direction of the handle or of the attachment part, and thus to permit the unlocking movement of the arresting piece transverse to the longitudinal direction of the handle. Advantageously, the two driving surfaces are measured and matched to one another in the transverse direction, i.e. transverse to the longitudinal direction of the handle or of the attachment part, in such a way that in the non-arresting position of the arresting piece they overlap one another and abut one another, but are offset to one another in the transverse direction in the arresting position of the arresting piece. In other words, when the attachment part is removed, the named driving surfaces move out of engagement at the latest towards the end of the axial movement of the arresting piece on the handle, in order to enable a complete removal of the attachment part.

The abutting surface on the attachment part is advantageously situated immediately bordering the edge of the recess into which the arresting piece on the handle can enter. In particular, the named abutting surface can move in flush fashion into the recess edge surface, and/or can simultaneously at least partially form the latter recess edge surface. Advantageously, the named abutting surface is situated on that edge segment of the recess that, when viewed in the longitudinal direction of the attachment part, is situated deepest in the tube-shaped attachment piece of the attachment part.

Advantageously, the named driving surfaces for the driving of the arresting piece during the removal of the brush attachment can be formed on the one hand by a recess edge surface of the recess provided on the attachment part, and on the other hand by an edge surface of the snap projection on the arresting piece on the handle.

Alternatively, or in addition, the named abutting and driving surfaces can also be provided on a snap element that is provided for the snap connection of the attachment part onto the handle neck, wherein the named snap element is also advantageously independent of the attachment of the named abutting and driving surfaces. In particular, this snap element can have a snap hook that enters into the interior space of the handle neck when the attachment part is pushed onto the toothbrush handle, and there snaps onto a snap contour on the handle when the fully attached position has been reached.

However, alternative to such a snap hook that moves into the interior of the handle neck, a snap hook can also be advantageous that moves over the outer jacket surface of the handle neck and snaps on a snap contour provided there and/or also on the arresting piece that is extended there.

Here, the named snap hook can advantageously be designed in the form of a spring clip that is movable transverse to the longitudinal direction of the attachment part, which is in particular radially movable, and whose longitudinal axis advantageously extends essentially parallel to the longitudinal direction of the attachment part. At its free end, this spring clip has a suitable snap contour, for example in the form of a projecting snap nose or a concave snap recess.

Such a snap element additionally secures the attachment part on the handle neck, which can be advantageous in particular if the arresting means is axially pre-tensioned away from the grip segment of the handle by means of a pre-tension device, so that the pre-tension force can be compensated by the snap connection. In order to, on the one hand, enable a secure snap connection, while on the other hand enable an easy disengagement of the snap connection when the brush attachment is removed, there can be provided on the snap element, for example on the snap hook, and/or on the arresting piece, an oblique surface that acts as a wedge surface and that disengages the snap connection when, during the removal of the brush attachment, the arresting piece undergoes the previously described actuation relative to the handle neck.

Alternatively or in addition to a snap element in the form of a snap hook, a snap contour can also be designed in the window-type recess in the connecting piece of the attachment part with which the arresting piece snaps when it is moved into its position in which it is disengaged from the drive shaft. Advantageously, a pair of snap contours, which are undercut in the radial direction, can be provided in particular on the connecting piece, preferably in the form of snap projections that move into engagement with complementary snap contours on the side flanks of the arresting piece, in particular with a pair of snap depressions arranged on opposite sides of the arresting piece when the arresting piece moves, in the manner described above, into the window-type recess of the connecting piece of the brush attachment.

In order to ensure an attachment and connection with a precise fit of the attachment part onto the toothbrush handle even when there is dirt on the fit surfaces, dirt receptacle depressions are provided on the handle neck of the toothbrush handle and/or on the connecting piece of the attachment part, into which dust particles, crumbs, or the like can, so to speak, slide when the two toothbrush parts are placed on one another, so that they do not hinder the coupling process. The named dirt receptacle depressions can here be provided in particular on the cylindrical or conical fit surfaces of the handle neck and the attachment part, in particular on the outer jacket surface of the handle neck and on the inner jacket surface of the connecting piece of the attachment part. Alternatively, or in addition, such dirt receptacle depressions can also be provided on the arresting piece of the toothbrush handle and/or of the attachment part and/or on the engagement parts provided thereon, so that the coupling process is not hindered. For example, the outer surface of the spreadable arresting piece and/or the inner surface, which can be brought into engagement therewith, of the attachment part can be provided with such dirt receptacle depressions, so that the spreading of the arresting piece is not hindered.

The named dirt receptacle depressions can be designed in various ways. According to an advantageous embodiment, the named dirt receptacle depressions can be designed in the form of a surface ribbing, in particular in the form of a longitudinal ribbing having essentially channel-shaped receptacle depressions that run in the longitudinal direction of the toothbrush.

These and further features, which, independent of their summarization in the claims, can form the subject matter of the present invention alone, in subcombination, or in combination with one another, arise both from the claims and from the following description and the associated drawings.

Figure 2:
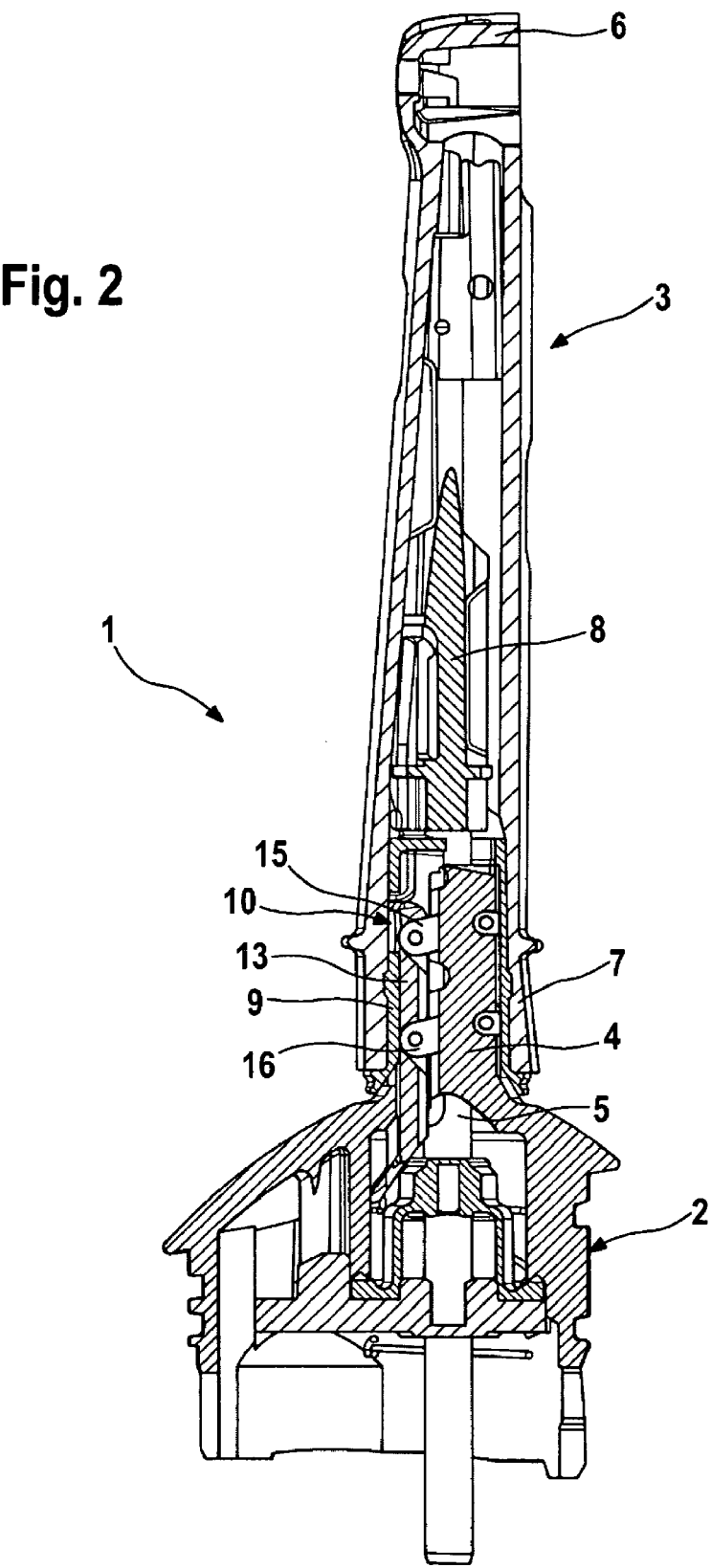
Figure 3:
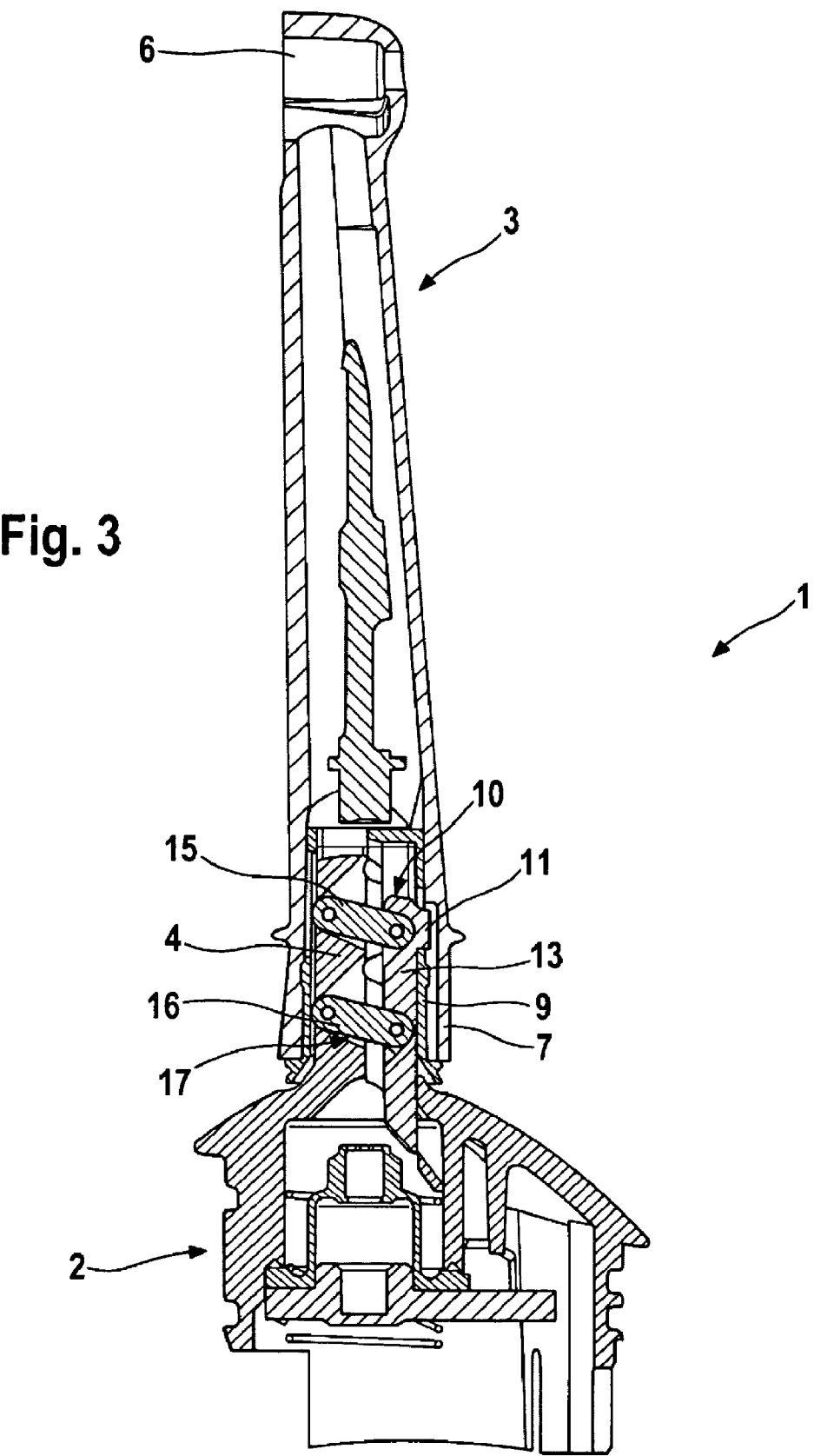
Figure 4:
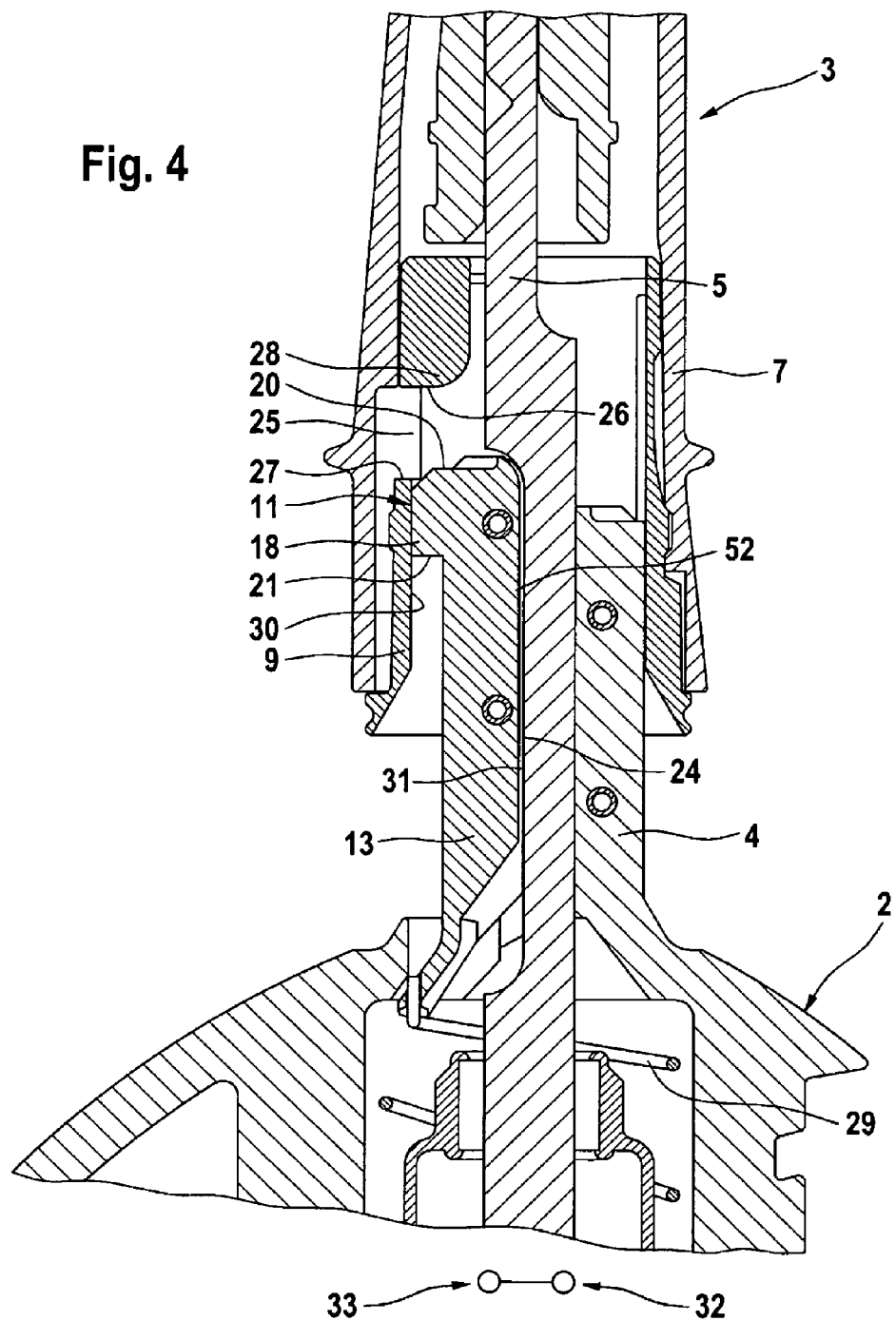
Figure 5:
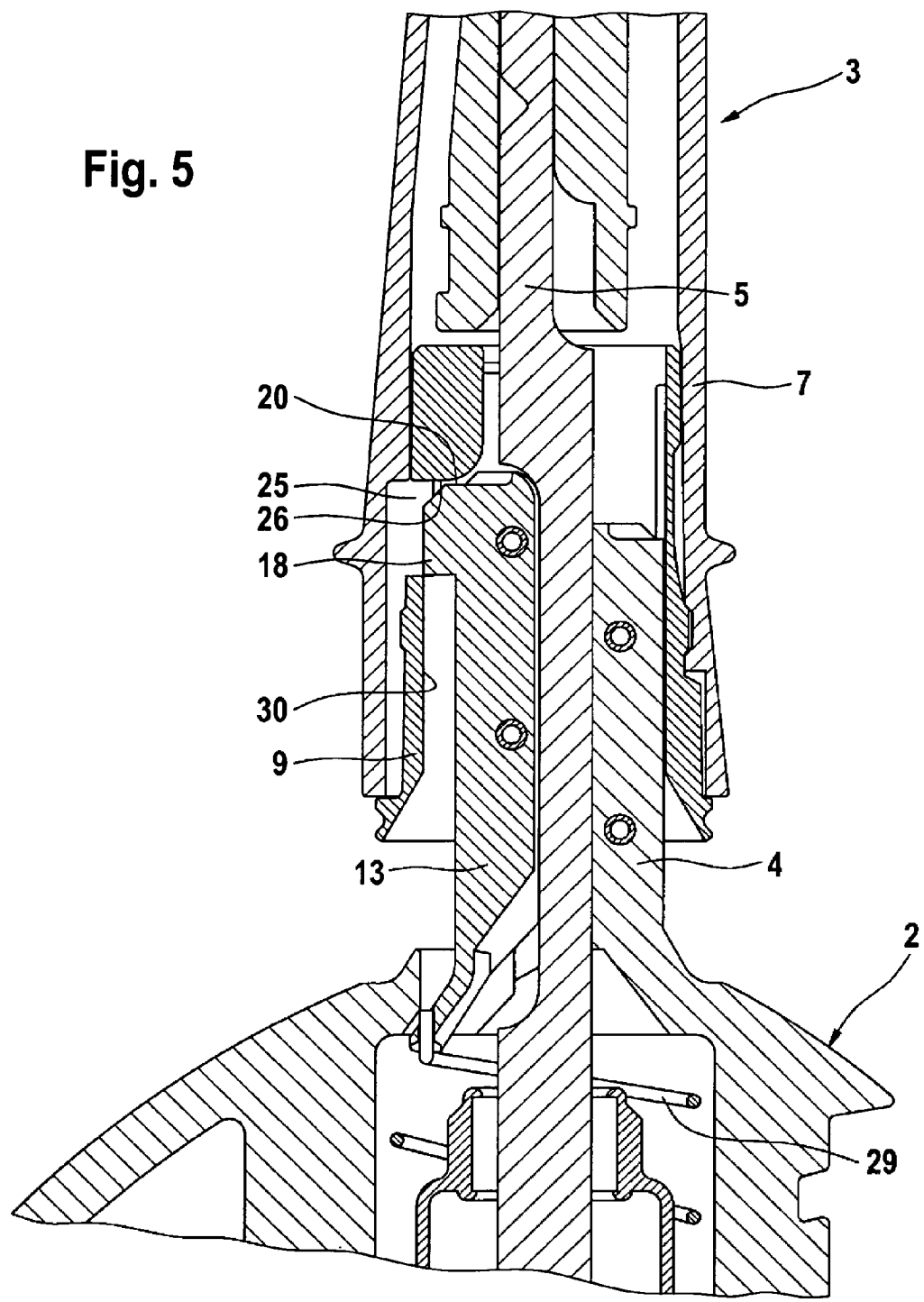
Figure 6:
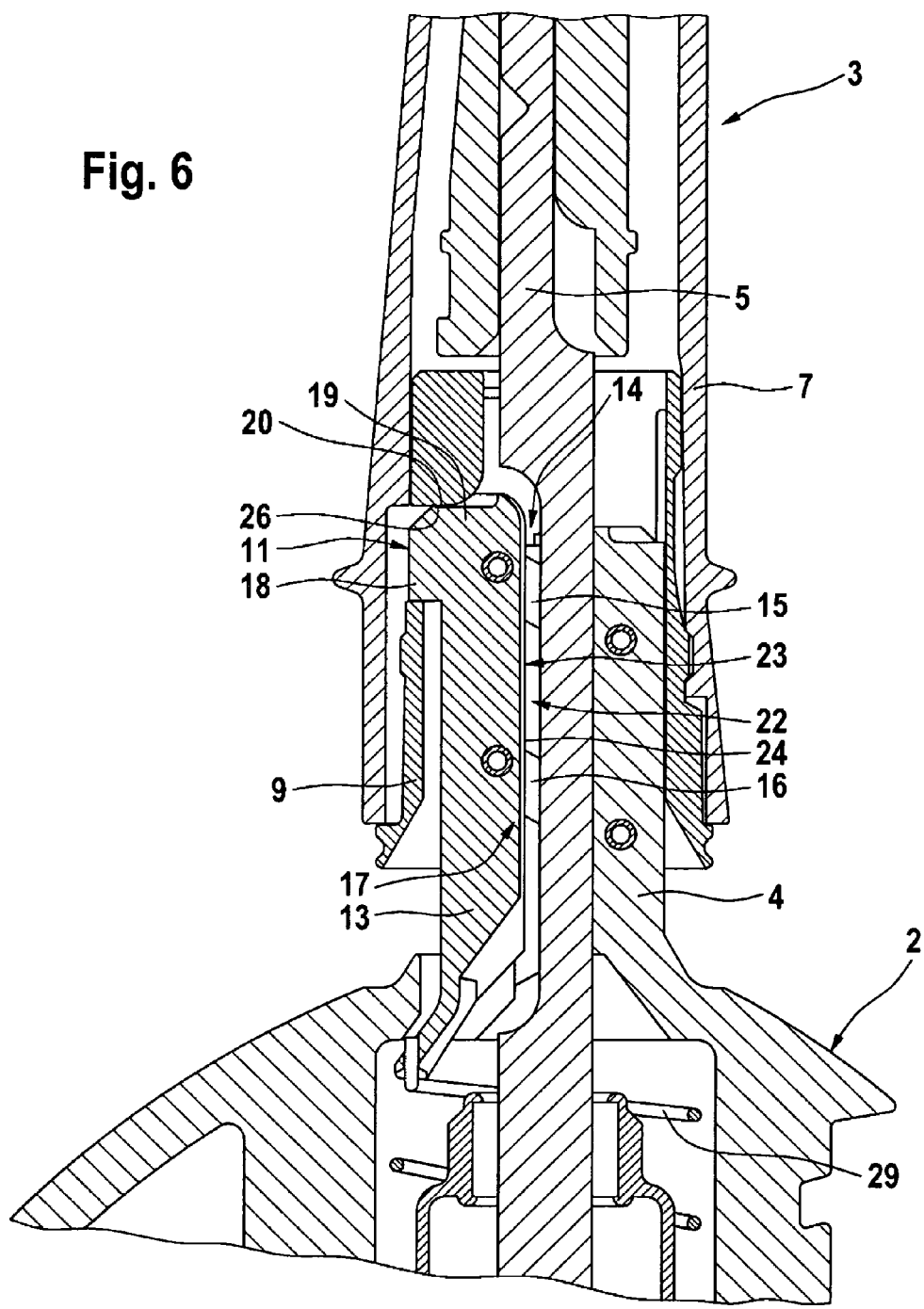
Figure 7:
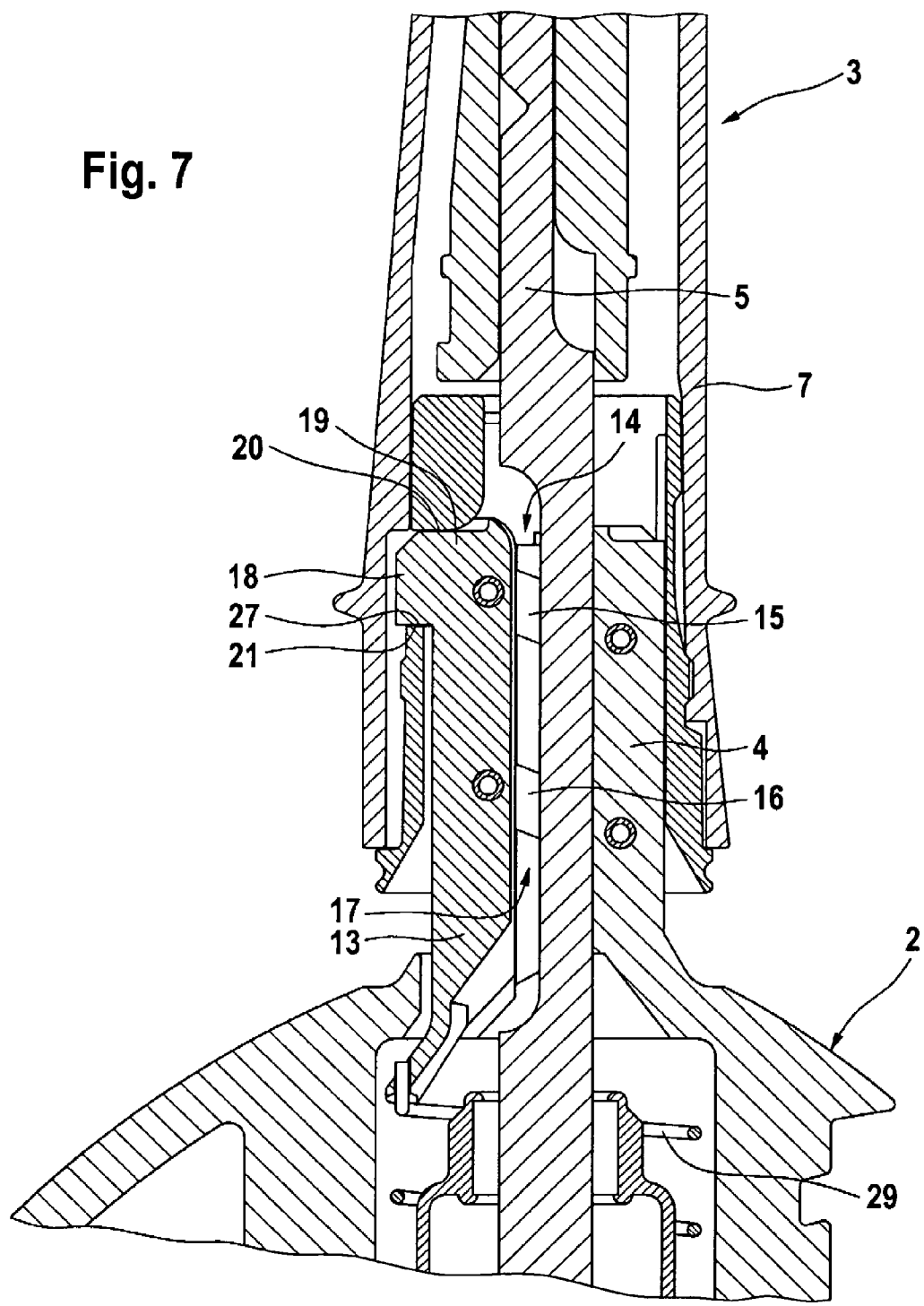
Figure 8:
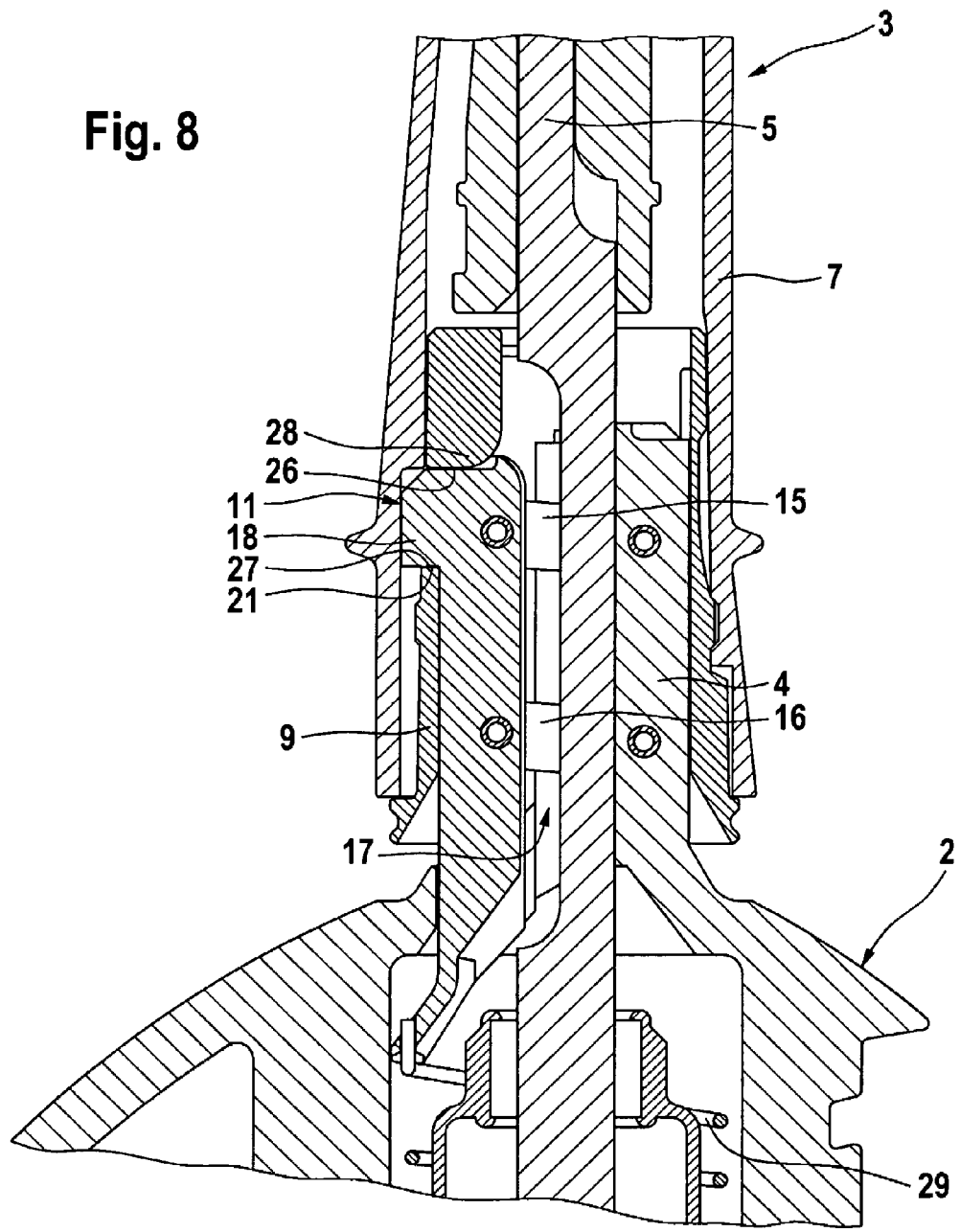
Figure 9:
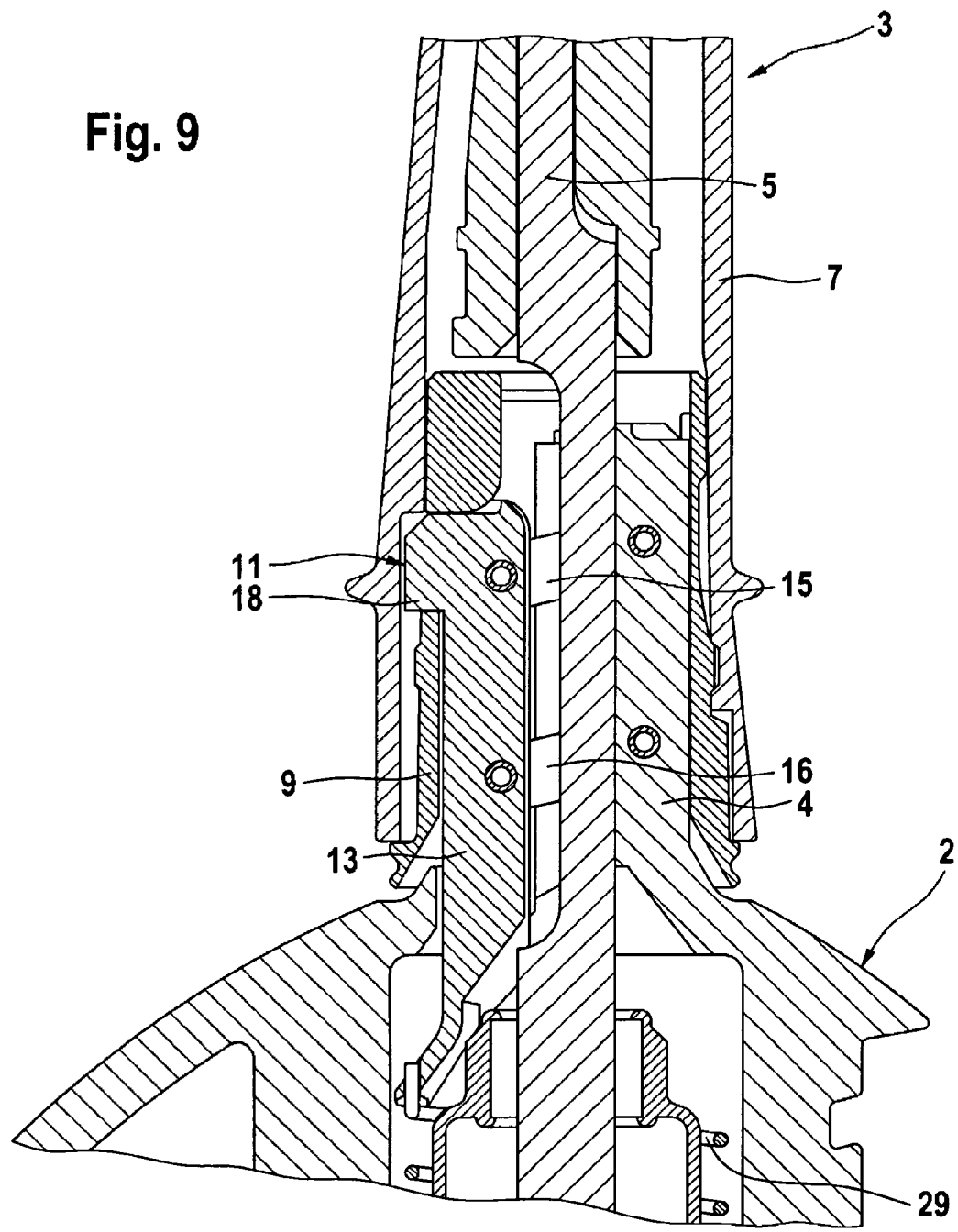
Figure 10:
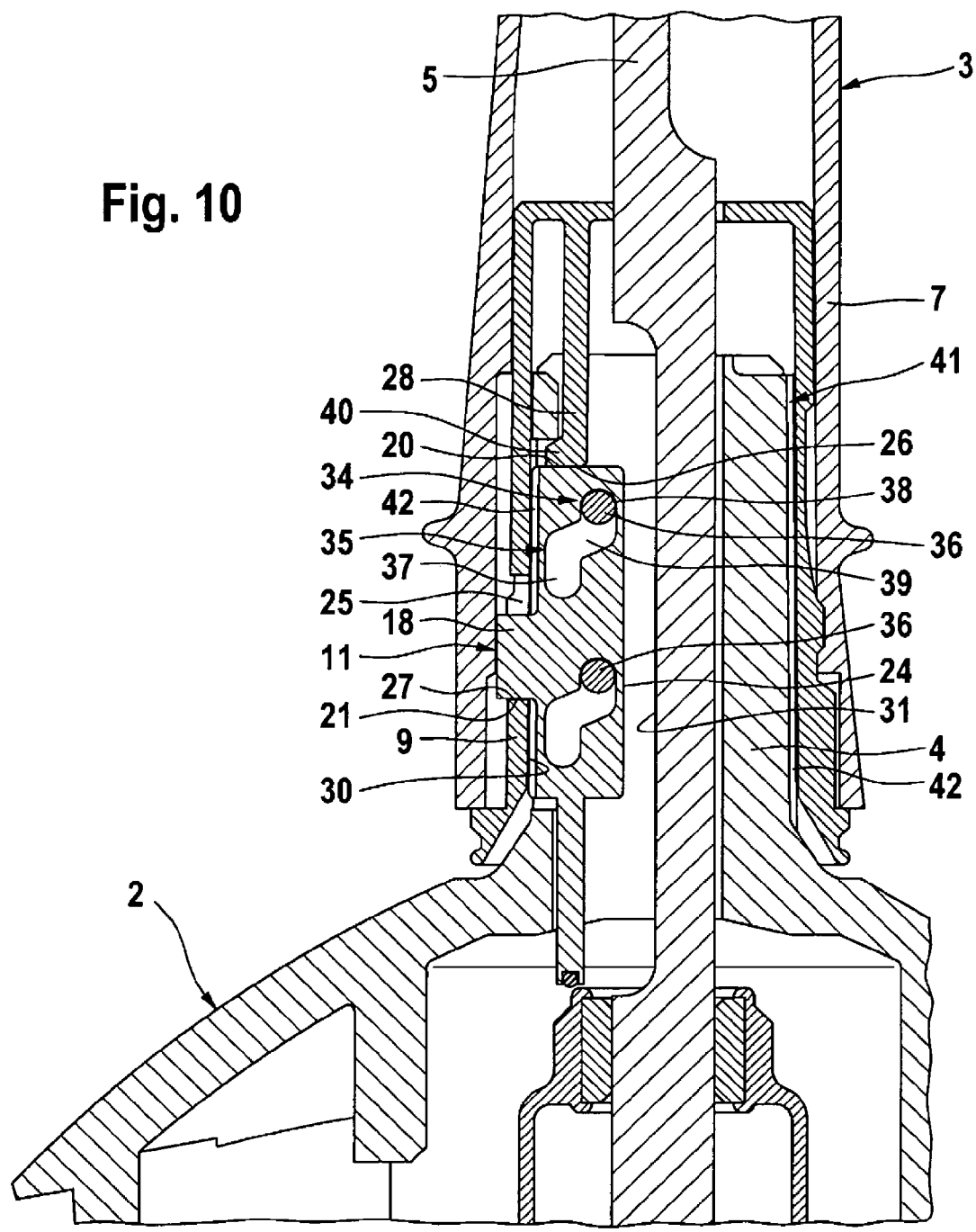
Figure 11:
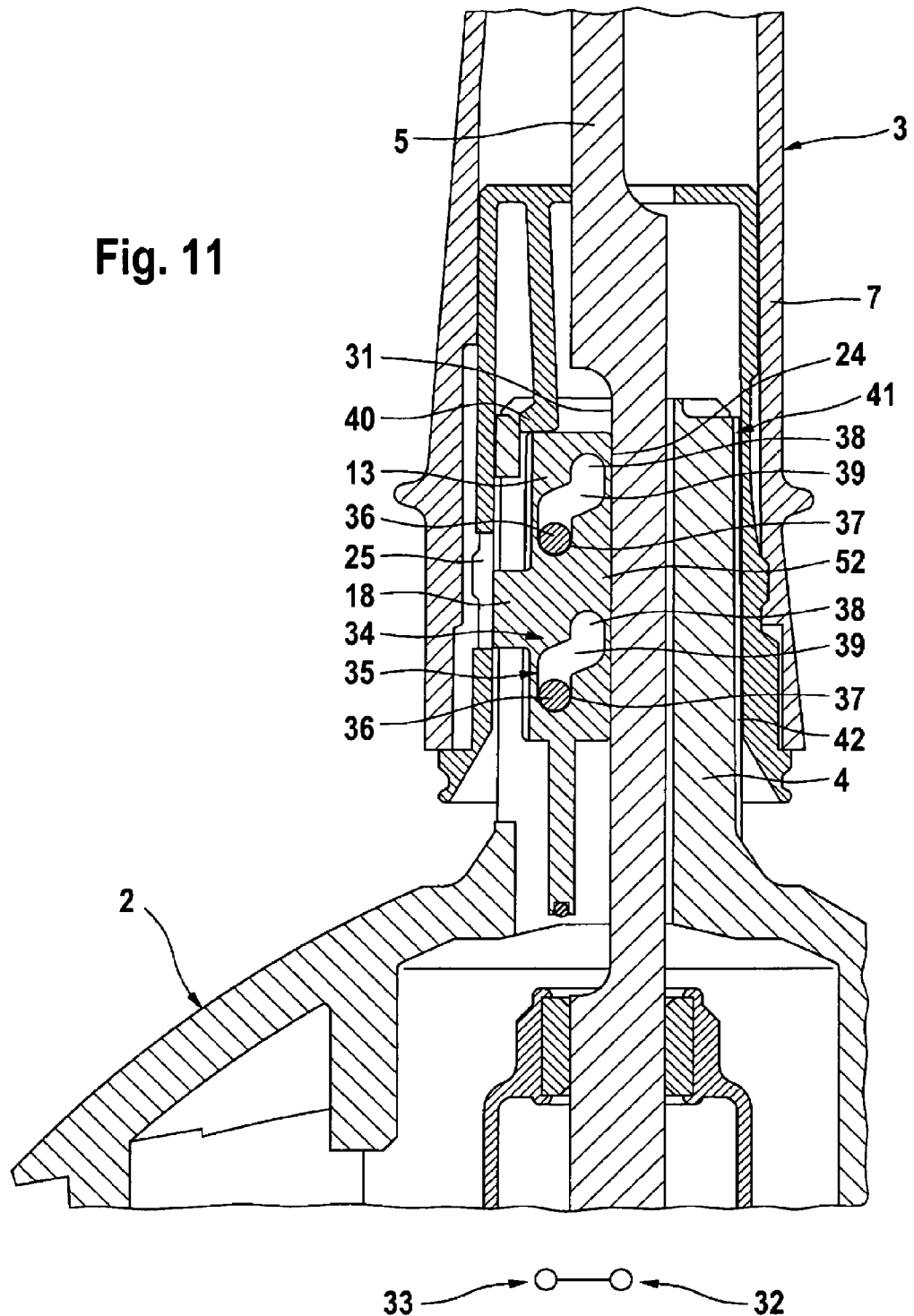
Figure 12:
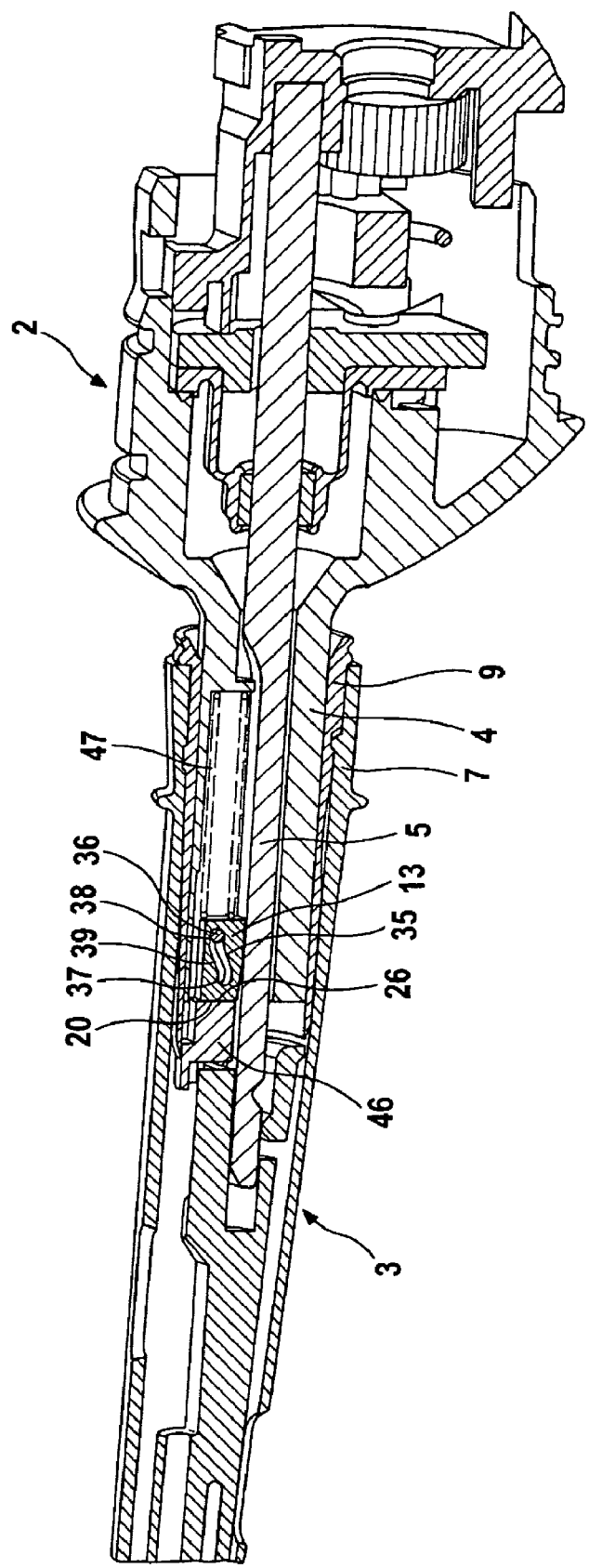
Figure 13:
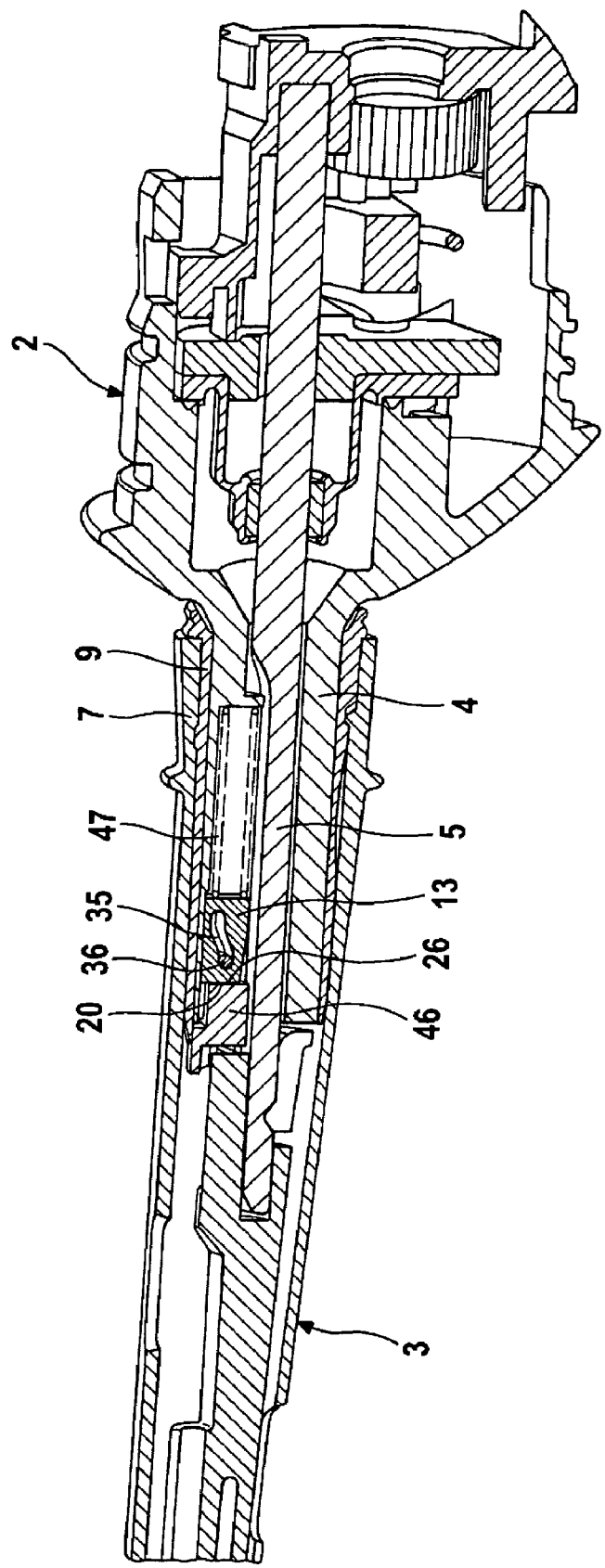
Figure 14:
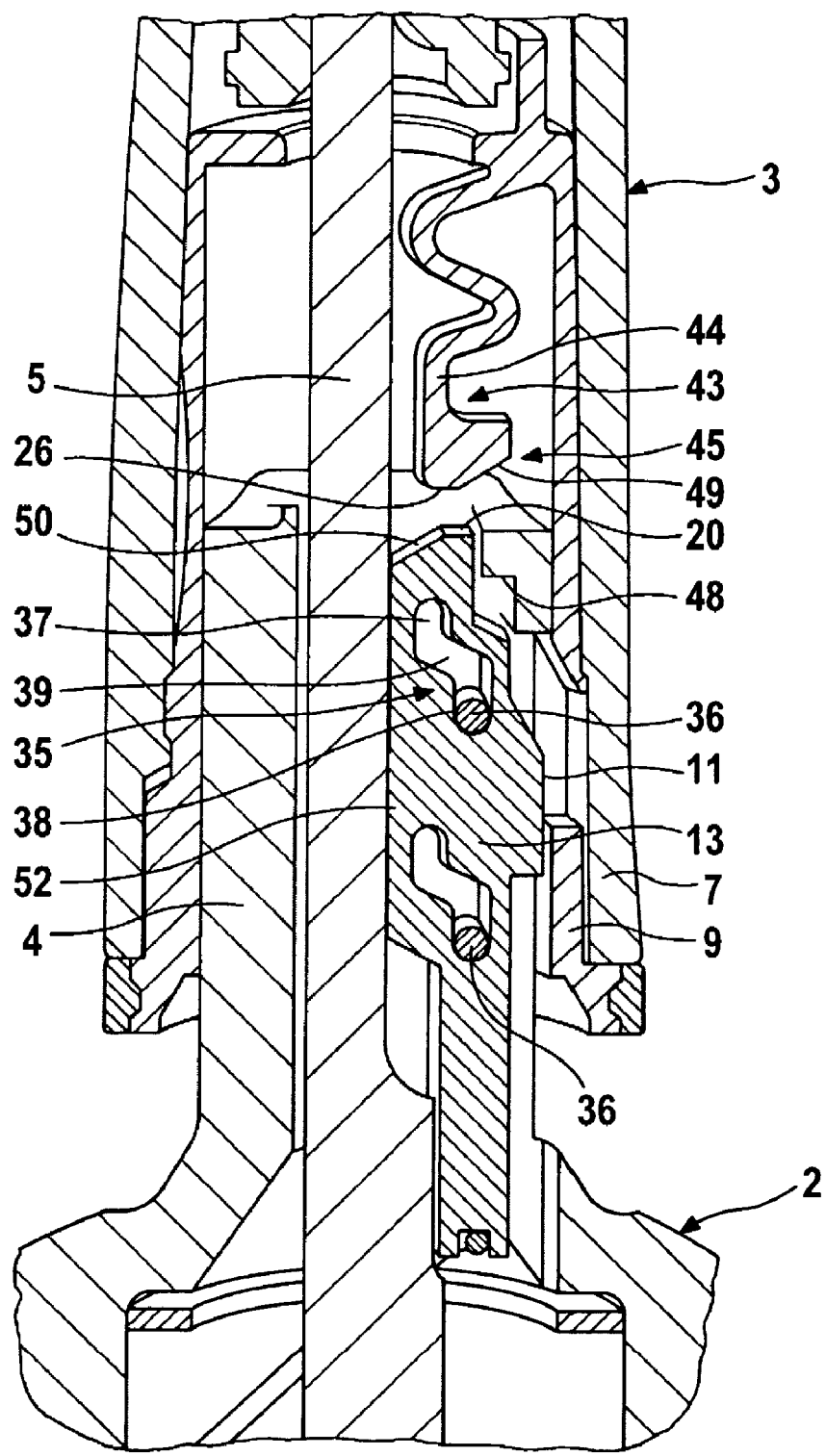
Figure 15:
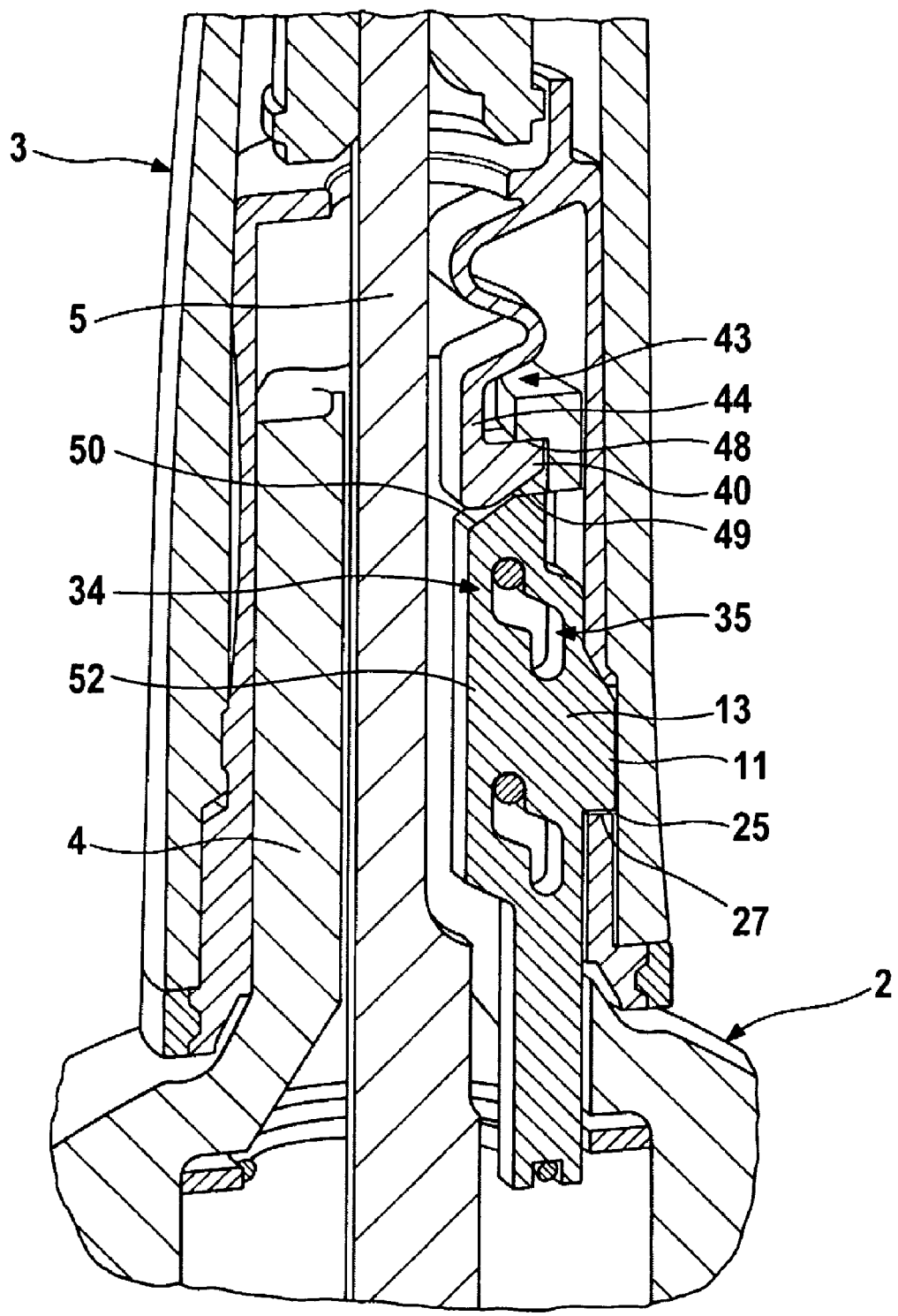
Figure 16:
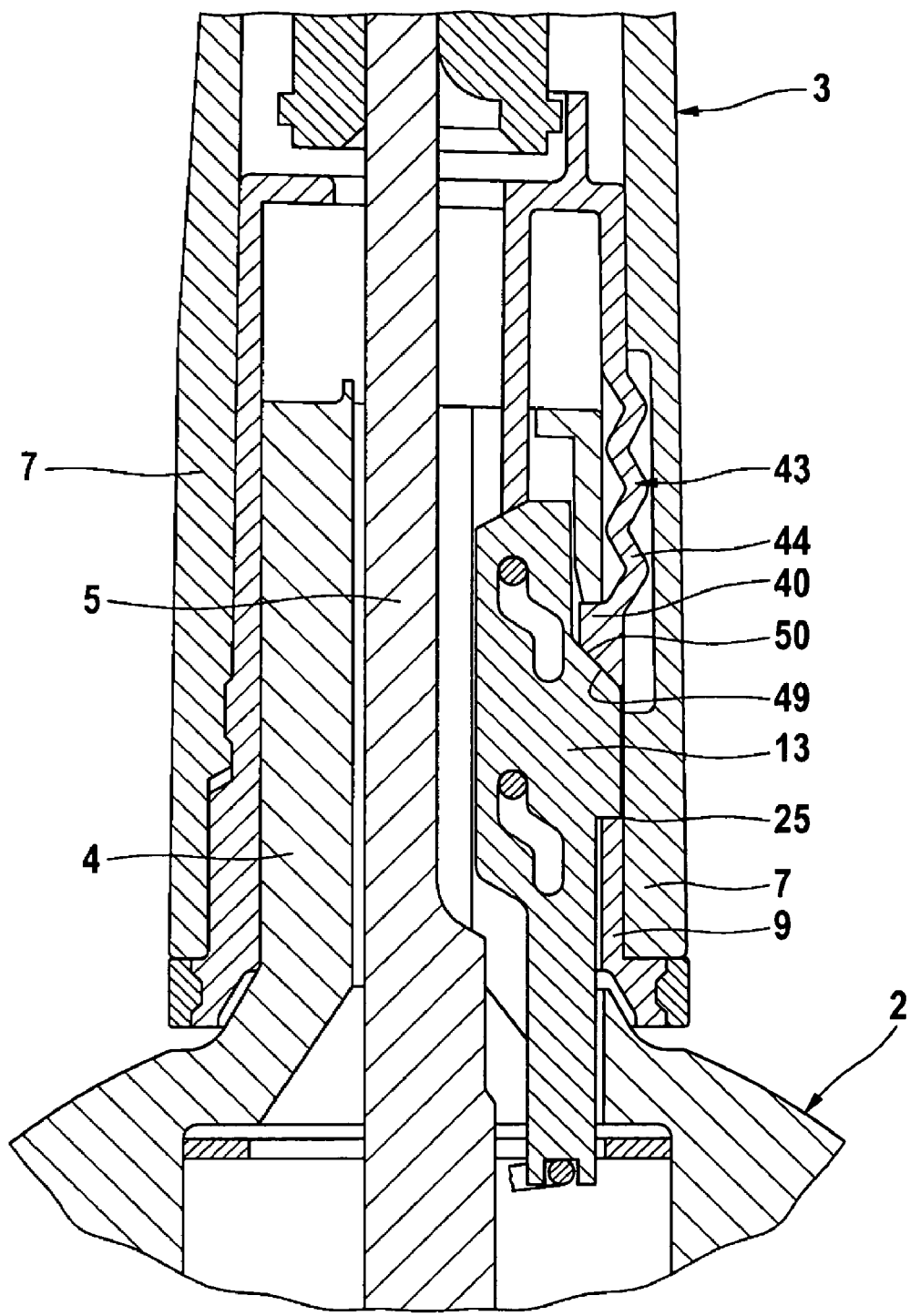
Figure 17:
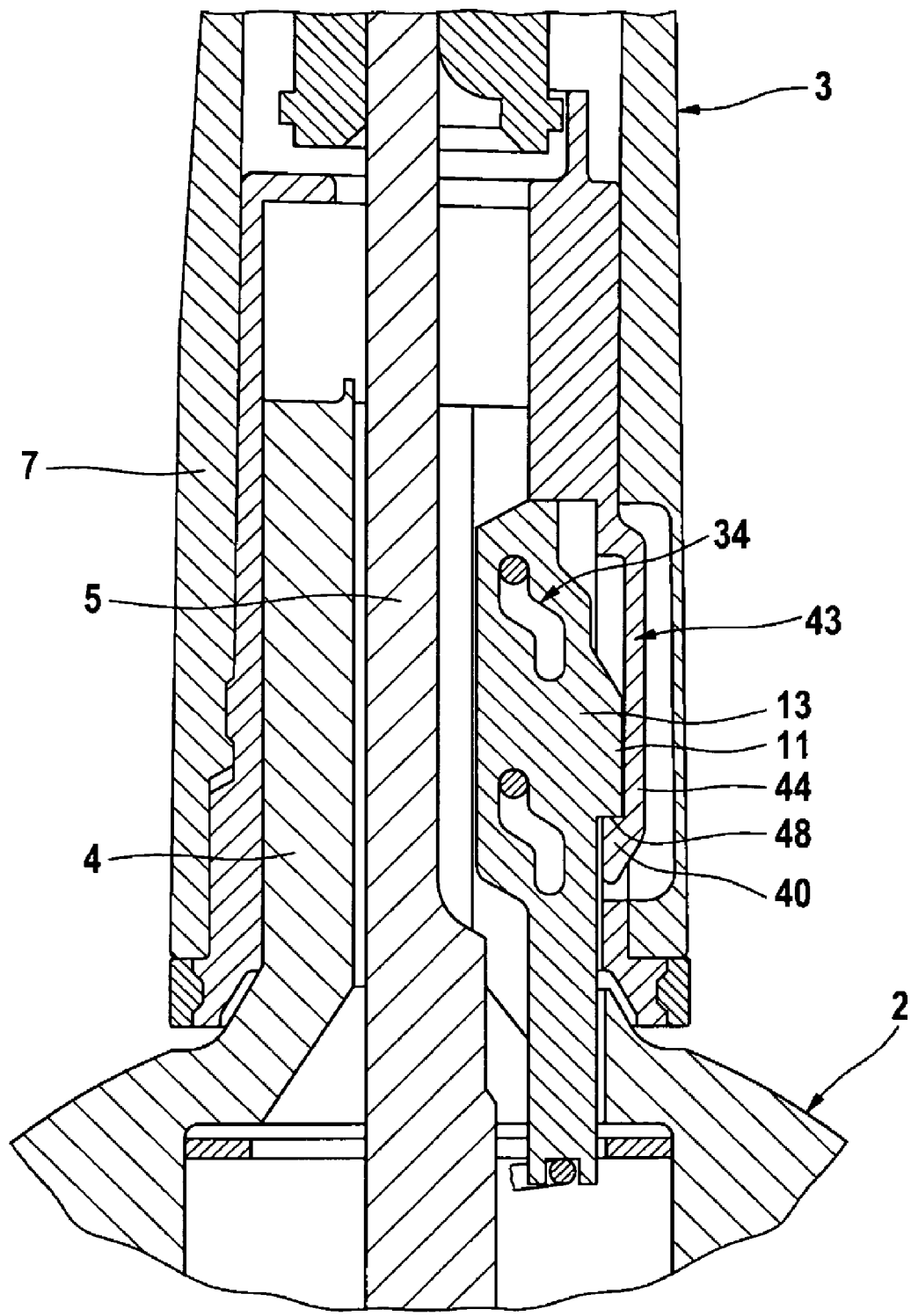
Figure 18:
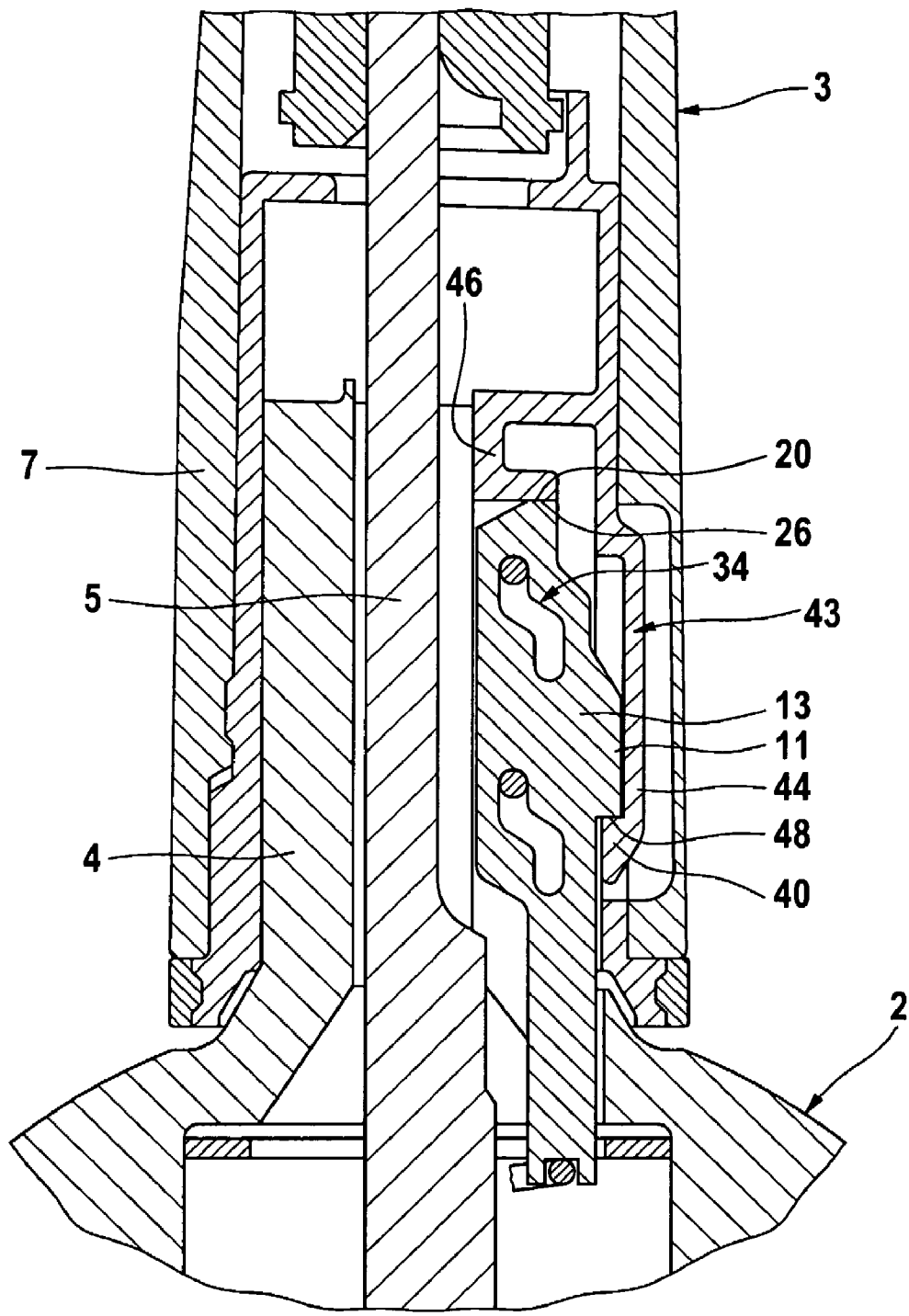
Figure 19:
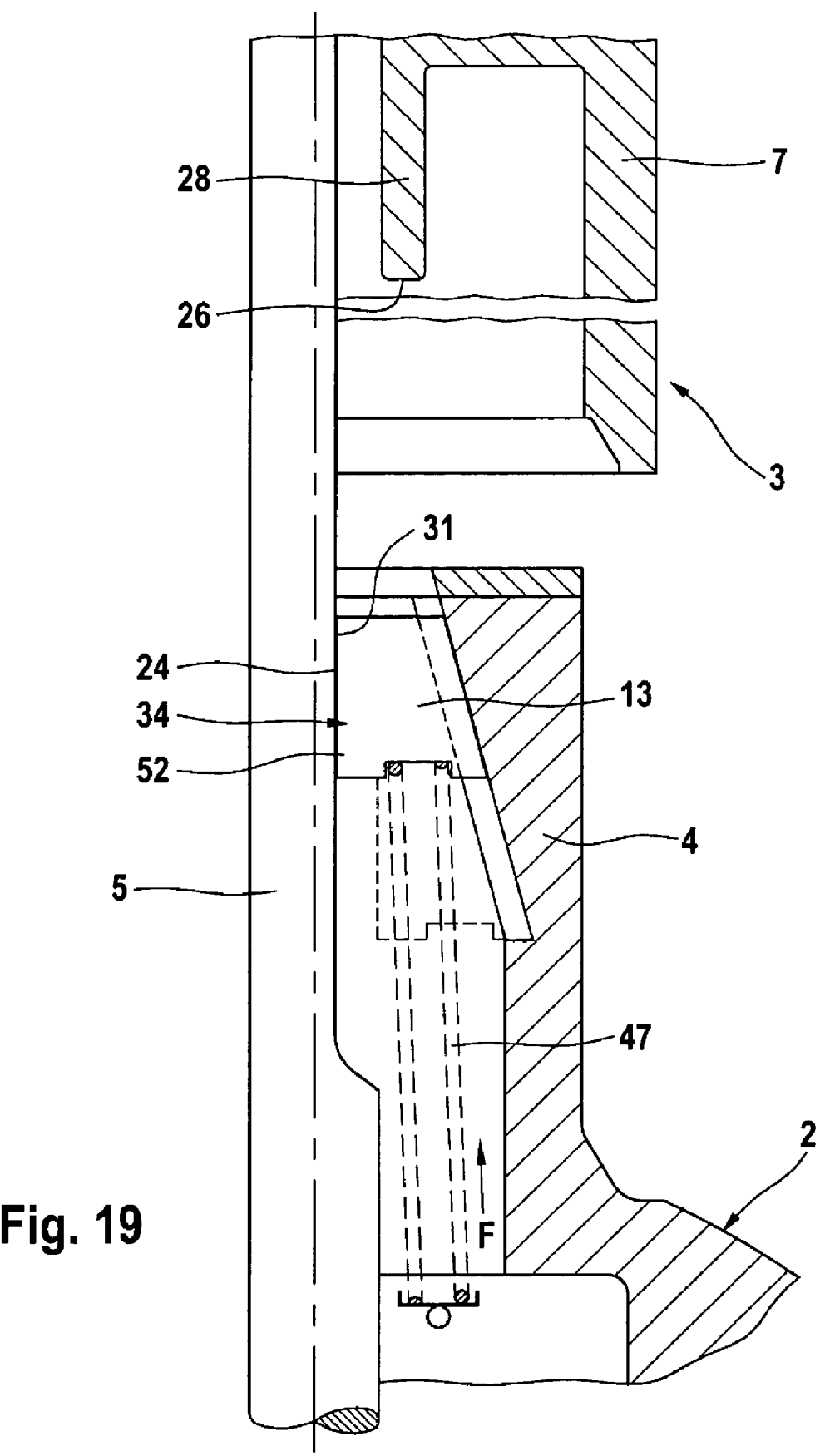
Figure 20:
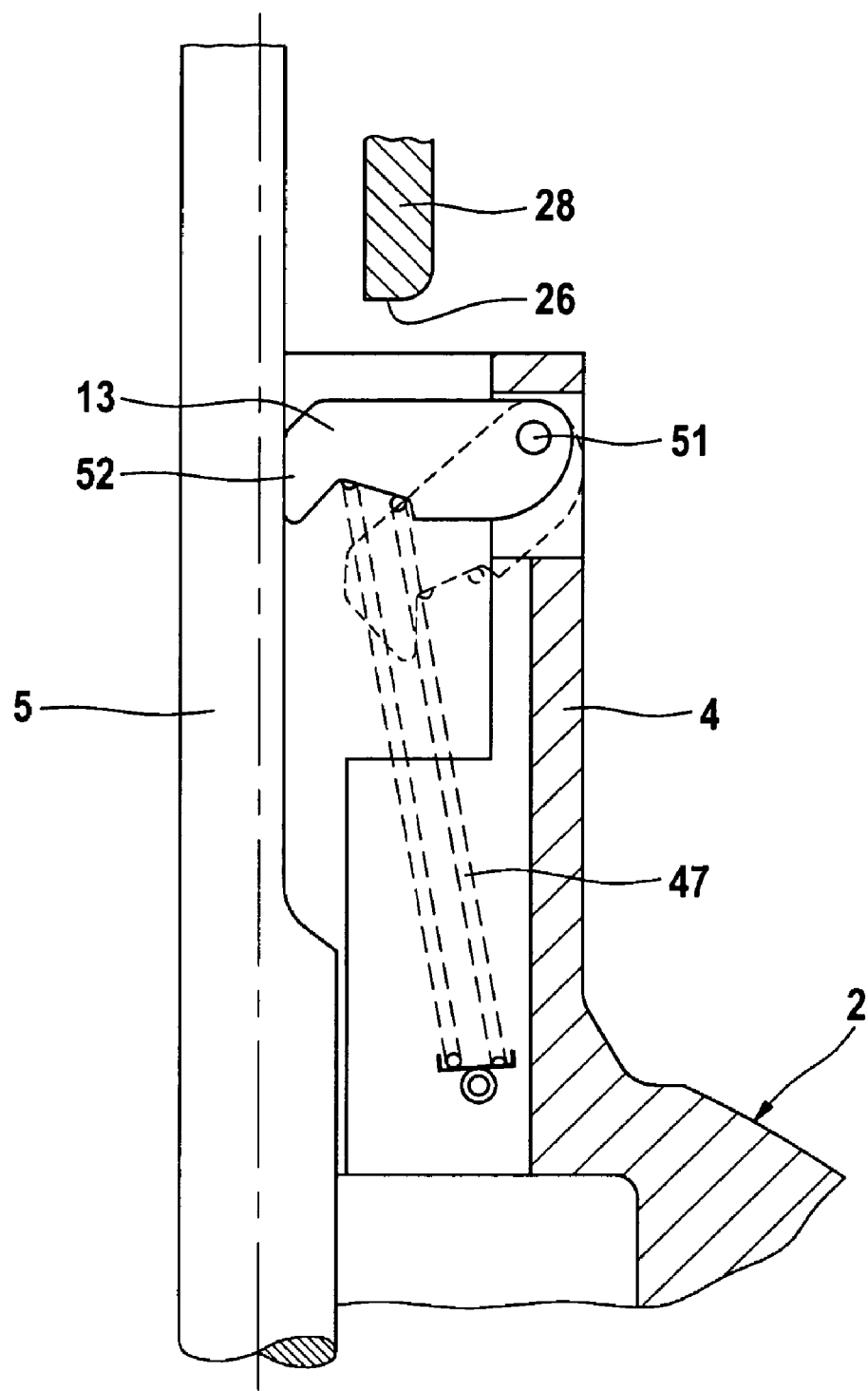
Figure 21:
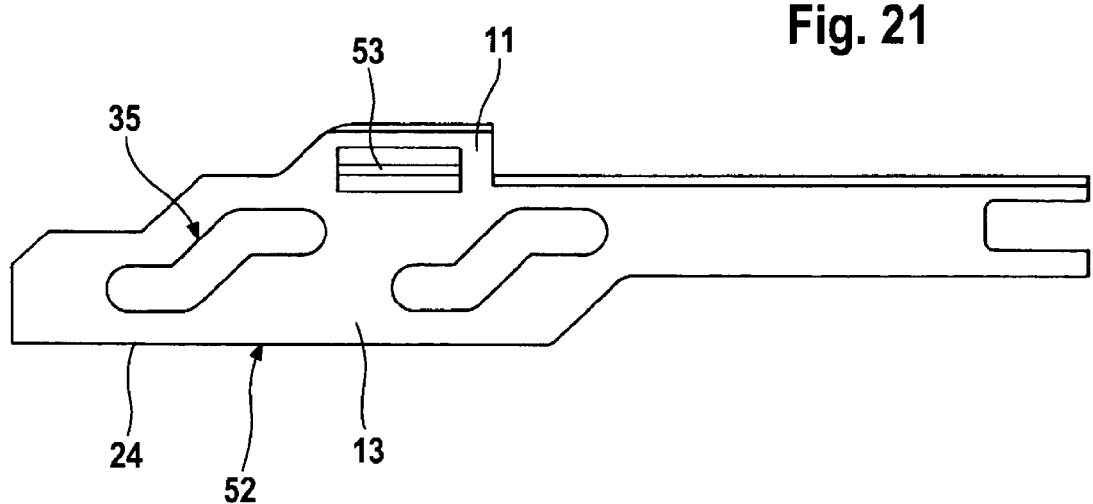
Figure 22:
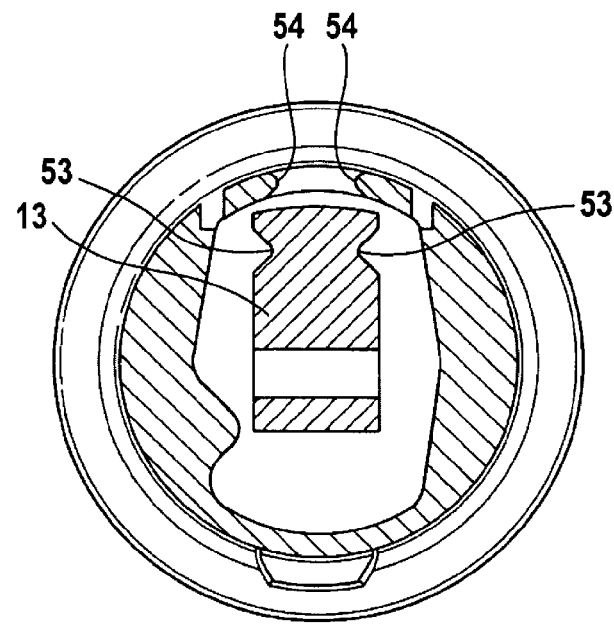

FIG. 1 shows a top view of a segment of an electric toothbrush according to a preferred embodiment, which shows its brush attachment and a segment of its handle, FIG. 2 shows a longitudinal section by means of the toothbrush from FIG. 1 along the line C-C depicted therein, which shows the handle neck, which has a two-part construction, with the arresting piece provided thereon in its non-arresting position, FIG. 3 shows a longitudinal section by means of the toothbrush from FIG. 1 along the line B-B depicted therein, which shows the parallelogram rod guide of the arresting piece on the handle, FIG. 4 shows a schematic sectional view of a toothbrush from the preceding Figures, which show the connecting piece of the brush attachment while attaching onto the handle neck, wherein the arresting piece on the handle is still in its arresting position, FIG. 5 shows a schematic sectional view of a toothbrush from the preceding Figures, similar to FIG. 4, which show the attaching of the brush attachment in a position shortly before the arresting piece reaches an abutting surface in the connecting piece of the brush attachment and is actuated, FIG. 6, FIG. 7, and FIG. 8 show further positions of the arresting piece on the handle during further attaching of the brush attachment onto the toothbrush handle in a schematic longitudinal section of a segment of the toothbrush, similar to FIGS. 4 and 5, FIG. 9 shows the non-arresting end position of the arresting piece on the handle in the fully attached position of the brush attachment, in a schematic longitudinal sectional view of a segment of the toothbrush, similar to the preceding FIGS. 4 through 8, FIG. 10 shows a longitudinal section of a toothbrush, similar to FIG. 4, according to a further advantageous embodiment according to which the arresting piece can be spread via a sliding block guide, wherein the named arresting piece is shown in its extended, non-arresting position, FIG. 11 shows a longitudinal section by means of a toothbrush from FIG. 10, wherein the arresting piece is shown in its retracted position in which it arrests the drive shaft, FIG. 12 shows a longitudinal section by means of a toothbrush, similar to FIGS. 10 and 11, according to a further advantageous embodiment, according to which an arresting piece designed as a sliding block is provided that is guided in a slotted link by means of only one guide pin, wherein FIG. 12 shows the position in which the drive shaft is locked, FIG. 13 shows a longitudinal section of the toothbrush from FIG. 12, wherein the sliding block is shown in its non-arresting position, FIG. 14 shows a longitudinal section by means a toothbrush, similar to FIGS. 10 and 11, according to a further advantageous embodiment, according to which the brush attachment has a snap hook, designed as a spring clip, for making a snap connection to the handle neck, said hook simultaneously form a ram for actuating the arresting piece guided in a sliding block guide, wherein the named arresting piece is shown in its position in which it locks the drive shaft, and the named snap hook is shown in a not-yet-snapped-in position, FIG. 15 shows a longitudinal section of the toothbrush from FIG. 14, wherein the named snap hook is shown in a snapped-in state and the arresting piece is shown in its non-arresting position, FIG. 16 shows a longitudinal section by means of a toothbrush similar to FIG. 14, according to a further advantageous embodiment according to which the snap hook travels over the outer periphery of the handle neck and snaps in on its outer periphery, FIG. 17 shows a longitudinal section by means of a toothbrush similar to FIG. 16, according to a further advantageous embodiment according to which the snap hook provided on the brush attachment travels over the outer periphery of the handle neck and snaps with the outwardly spread arresting piece in order to lock the drive shaft when the named arresting piece according to FIG. 17 is in its spread, non-arresting position, FIG. 18 shows a longitudinal section by means of a toothbrush, similar to FIG. 17, according to a further advantageous embodiment according to which in addition to the snap hook that snaps with the arresting piece, a pressure or blocking piece is provided on the connecting piece of the brush attachment that holds the arresting piece in its attached position against a spring force, FIG. 19 shows a schematic longitudinal section by means of a toothbrush, similar to the preceding Figures, according to a further advantageous embodiment according to which the arresting piece is guided so as to be capable of longitudinal displacement in a dovetail channel guide for the arresting of the drive shaft, and is pre-tensioned into its arresting position by a spring device, FIG. 20 shows a schematic longitudinal section by means of a toothbrush, similar to the preceding Figures, according to a further advantageous embodiment according to which the arresting piece is designed in the form of a pivotably mounted cam for the arresting of the drive shaft, FIG. 21 shows a side view of an arresting piece that is capable of being displaced in a sliding block guide, having a snap contour that is undercut in the radial direction of the toothbrush handle for making a snap connection with the brush attachment, and FIG. 22 shows a cross-section of the toothbrush in the area of the named snap contour of the arresting piece, showing the depression-shaped formation thereof on the arresting piece, and showing the snap contours that cooperate therewith on the attachment part.

Toothbrush 1 shown in the Figures comprises a handle 2 and an attachment part connected thereto in the form of a brush attachment 3. The handle 2, shown only partially, comprises in a known manner a housing in which a drive motor and an energy supply device, for example in the form of an accumulator, and on which an actuating switch is provided for switching the drive on and off are located. On the frontal end, shown in FIGS. 1 through 3, of the handle 2, the housing of the handle 2 forms a handle neck 4 that in the depicted embodiment—in an overall view—is designed in the form of a connecting piece that protrudes at a frontal end and is stub-shaped and essentially cylindrical, and that may optionally have a slight conical taper toward its free end. A drive shaft 5 that is capable of being driven in rotationally oscillating fashion protrudes from the frontal end of named handle neck 4.

The brush attachment 3 comprises an operating head 6 having a field of bristles that is not shown in more detail, and that in the depicted embodiment is capable of being driven in rotationally oscillating fashion about a bristle field axis that is oriented approximately in the longitudinal direction of the bristles. Said operating head 6 is carried by a connecting piece 7 that is tube-shaped overall and that is capable of being attached onto the handle neck 4 of the toothbrush handle 2. In the interior of named tube-shaped connecting piece 7, the brush attachment 3 has a attachable shaft 8 that can be coupled in rotationally fixed fashion to the drive shaft 5 on the handle.

In order to fasten the brush attachment 3 to the handle 2, a coupling insert 9, in the form of a coupling sleeve or coupling ring, is provided in or on tube-shaped connecting piece 7, which is situated in or on the tube-shaped connecting piece 7 so as to be axially and/or radially firmly seated. Roughly stated, named coupling sleeve 9 is designed so as to be cylindrical or slightly conical overall, so that the coupling sleeve 9 can be pushed axially onto the handle neck 4, whereby a largely clearance-free fastening of the brush attachment to the handle 2 can be achieved. In another embodiment of a plug-on brush, the connecting piece 7 is constructively combined, i.e. designed in one piece, with the coupling insert 9.

As FIGS. 2 and 3 show, a rib-shaped and/or approximately half-shell-shaped arresting piece 13 is provided on the handle neck 4 of the toothbrush handle 2 that on the one hand forms an arresting means 23 for blocking the drive shaft 5, and simultaneously forms a coupling piece of a coupling device 10 on the handle that can be brought into locking engagement with the coupling insert 9 on the brush attachment. Here, the stub-shaped handle neck 4 is, so to speak, divided into two parts, into a body part that is connected rigidly to the handle housing, forming the actual handle neck 4, and the movably mounted arresting and coupling piece 13, which, in the initial position in which it arrests the drive shaft 5, as shown for example in FIG. 4, essentially continues the contour of the handle neck 4 and forms together therewith the connecting stub onto which the tube-shaped connecting piece 7 can be attached.

The arresting and coupling piece 13 on the handle, whose plane of symmetry extends in longitudinal direction 12 of the handle 2, is movably coupled to the handle neck 4 by a parallelogram rod guide 17. As FIG. 3 best shows, the parallelogram rod guide 17 comprises two pivotable rods 15 and 16 that are oriented parallel to one another and that are linked at their one end to the handle neck 4 and at their other end to the arresting piece 13. The "two" rods 15 and 16 may also be two rod pairs arranged to the left and right respectively of the drive shaft 5, and coupled via respective common pairs of pivot axes, so that the arresting piece 13 is also supported stably against tilting transverse to the rods.

As shown in a comparison of FIGS. 4 through 9, the arresting piece 13 can be pivoted or moved back, via the parallelogram rod guide 17, from a front end position situated at the frontal end of the handle and the blocking drive shaft 5, forming so to speak the initial position, toward the handle 2 into a second end position in which the brush attachment is locked on the handle neck. Here, the parallelogram rod guide 17 forms a spread mechanism 14 that spreads the arresting piece 13 transverse to the longitudinal direction of the toothbrush when it is moved from the front end position into the rear end position, so that, as FIG. 9 shows, in the second end position arresting piece 13 stands radially further outward than it does in the front, first end position, shown in FIG. 4. Here, the diameter of the coupling insert 9 of the brush attachment 3 is advantageously matched so as to fit the spread movement of the arresting piece 13, so that when there is excess pressure on the parallelogram guide rod 17 a slight elastic deformation occurs, and/or a tightly seated fit with slight radial pressure on the arresting piece 13 is achieved in the area around the position of the arresting piece 13 that locks the brush attachment 3. In this way, the brush attachment 3 is held stably on the toothbrush handle 2.

As shown FIGS. 4 through 9, the coupling insert 9 on the attachment part comprises on its inner jacket surface an outward-oriented recess 25 in the form of a window in the coupling insert 9, into which a radially protruding snap nose 18 on the arresting piece 13 can enter with a precise fit. Here, named snap nose 18 forms an engagement part 11 with which the coupling device 10 on the handle locks the brush attachment 3 on the handle neck 4.

On the coupling insert 9, a radially inward-protruding actuating projection 28 is advantageously provided in the vicinity of named recess 25; when the brush attachment 3 is attached onto the handle neck 4, said actuating projection drives the arresting piece 3 and presses it into its locking position. In the depicted embodiment, the actuating projection 28 is arranged behind the aforementioned recess 25, in the direction of attachment, wherein, when regarded radially, it protrudes further inward than does the segment 29, that is arranged in front of the recess 25 in the attaching direction, of the coupling insert 9; cf. FIG. 4. In the depicted embodiment, the actuating projection 28 is connected immediately to the recess 25, so that the abutting surface 20 on the actuating projection 28, extending transverse to the longitudinal direction of the attachment part, goes over into the recess edge surface in flush fashion; cf. FIG. 4.

In this way, the following function results: when the brush attachment 3 is attached onto the handle neck 4, at first the arresting piece 13 remains in its end position in which it is moved inward, which blocks the drive shaft 5. In its run-in area up to the recess 25, the coupling insert 9 has a clearance that, when viewed radially, is larger than the radial dimension of the snap nose 18 in the retracted, non-locking position of the arresting piece 13; cf. FIG. 4.

In this way, the brush attachment 3 can be pushed over the arresting piece 13 until its snap nose 18 comes to rest in the area of the recess 25, as is shown in FIG. 5. However, upon further pushing of the brush attachment 3, the abutting surface 20 on the frontal end of the arresting piece 13, which surface likewise extends transverse to the longitudinal direction 12 of the handle, abuts against the abutting surface 26 on the actuating projection 28 of the coupling insert 9. In this way, during the further attaching in of the handle neck, the arresting piece 13 remains, so to speak, stationary, and is spread outward by the parallelogram rod guide 17 on the movement path that is determined in this way, as is illustrated in FIGS. 6 through 8. The snap nose 18 correspondingly moves into the recess 25. When the brush attachment 3 has been fully attached, the perpendicular position shown in FIG. 8 of the rods 15 and 16 of the parallelogram rod guide 17 is advantageously traveled past, so that the dead point of the parallelogram rod guide 17 is overpressed. In the completely locked position, the rods 15 and 16 are inclined slightly back toward the handle 2; cf. FIG. 9.

When the brush attachment 3 is removed again, the arresting piece 13 is pivoted in the opposite direction back into its position in which it arrests the drive shaft 5. Here, an entraining surface 27 provided on the coupling insert 9 drives an driving surface 21 provided on the arresting piece 13, thus driving the arresting piece 13 in the axial direction. In the depicted embodiment, the driving surface 21 of the arresting piece 13 is formed by the rear side of the snap nose 18, and extends essentially perpendicular to the longitudinal direction 12 of the handle. On the coupling insert 9, the driving surface 27 is formed by an edge surface of the recess 25.

Here, the arresting piece 13 advantageously forms a control device 22, or a part thereof, that automatically prevents an unwanted activation of the toothbrush drive during the attaching and detaching of brush attachment 3. Here, the arresting piece 13 has on its inner side a flat area 24 that cooperates with a flat area 31 on the jacket surface of the drive shaft 5. As shown in a comparison of FIGS. 4 and 9, in the arresting position of the arresting piece 13 its flat area 24 is seated on the flat area 31 of the drive shaft 5, so that the latter cannot rotate. If, in contrast, the arresting piece 13 moves outward, the drive shaft 8 is released; cf. FIG. 9.

The named arresting of the drive shaft 5 can be a part of a travel safety and/or battery protection device that switches off the drive motor when the drive shaft is arrested. Using a suitable detection device, the named control device 22 can detect whether or not the arresting piece 13 is arresting the drive shaft 5. In particular, the detection means 32 can be provided for this purpose that detect the magnitude of the motor current. This is because when the drive shaft 5 is arrested, the motor current climbs above its normal level, so that when a predetermined motor current threshold is exceeded it can be assumed that this results from an arresting of the drive shaft 5, and thus a removed attachment part. A switch-off device 33 of the control device 22 can in this case shut off the drive motor in order to prevent damage to the drive motor or unwanted discharging of the battery.

As shown FIGS. 10 and 11, the spreading mechanism 14 for spreading the arresting piece 13 can also have, instead of the above-described parallelogram rod guide 17, a sliding guide in the form of a sliding block guide 34. In the depicted embodiment shown in FIGS. 10 and 11, here the arresting piece 13 comprises a guide slotted link 35 in the form of two guide channels, shaped as longitudinal channels and angled off in a stepped manner, into which two guide pins 36 engage whose diameter corresponds approximately to the width of the guide channels, in order to achieve an essentially clearance-free sliding guidance of the arresting piece 13. Instead of the two guide channels shown in FIGS. 10 and 11, it is also optionally possible to provide only one guide channel, in connection, optionally, with a further support of the arresting piece 13, so that during spreading, this arresting piece would additionally undergo a pivot movement. However, the slide block guide having two guide pins 36, shown in FIGS. 10 and 11, is preferred.

Advantageously, the named guide slotted link 35 can comprise guide segments 37, 38, and 39 that are differently inclined relative to the handle longitudinal direction 12, so that the stroke or spreading movement of the arresting piece 13 runs through a plurality of phases. Preferably, here a more steeply inclined center guide segment 39 is provided that opens into less strongly inclined guide end segments 37 and 38; cf. FIG. 10. The named guide end segments 37 and 38 are here advantageously oriented essentially parallel to the handle longitudinal direction 12, so that when the named guide pins 36 are arranged in the area of these guide end segments 37 and 38 no stroke movement of the arresting piece 13 takes place, and the arresting piece is held free of axial forces at the respective spread level. Optionally, the named guide end segments 37 and 38 can also be slightly inclined in the opposite direction, compared to the inclination of center guide segment 39, so that a slight excess pressure takes place when the end positions are approached.

The inclination of the center guide segment 39 is here advantageously matched to the particular characteristics of the coupling device 10, in particular the length of the attachment movement and the diameter of the handle neck, as well as the size of the flat area of the drive shaft 5, wherein in the specific embodiment depicted in FIG. 10, an angle of inclination in the range of approximately 45° to 80° has proven advantageous.

Apart from the construction of the spreading mechanism 14, the specific embodiment of FIGS. 10 and 11 corresponds essentially to the embodiment shown in the preceding Figures, so that in this regard reference is made to the preceding description, and the same reference characters are used for corresponding components.

With regard to function as well, the embodiment shown in FIGS. 10 and 11 corresponds essentially to the embodiment of the preceding Figures: when the brush attachment 3 is pressed onto the handle neck 4, at first the arresting piece 13 remains in its non-locking end position in which it is moved inward, as is shown in FIG. 11. The coupling insert 9 has in its run-in area up to the recess 25 a clearance that, when regarded radially, is greater than the radial dimension of the snap nose 18 of the arresting piece 13; cf. FIG. 11.

In this way, the brush attachment 3 can be pushed over the arresting piece 13 until its snap nose 18 comes to rest in the area of the recess 25. However, upon further pushing on of the brush attachment 3, the abutting surface 20 provided on an end surface of the arresting piece 13, and extending transverse to the handle longitudinal direction 12, abuts against the abutting surface 26 on the actuating projection 28 of the coupling insert 9. In this way, as the brush attachment 3 is further attached, the arresting piece 13 is axially driven, causing the arresting piece 13 to move in the sliding block guide 34. Here, the arresting piece 13 is pressed radially outward via the inclined center guide segment 39, so that the snap nose 18 of the arresting piece 13 enters into the window-type recess 25 of the brush attachment 3; cf. FIG. 10.

As show in FIGS. 10 and 11, here the actuating projection 28 of the brush attachment 3, which drives the arresting piece 13, is designed in the form of a spring clip that, in the fully attached position, snaps on the handle neck 4, forming to this extent a snap device, for example a snap hook. In particular, when moved into the interior of the handle neck 4 the snap hook can, at first, radially move away under a spring force and slide over a handle neck contour. When the end position is reached, the snap hook can snap into an undercut recess, moving back under spring force. In the depicted embodiment, here the spring hook is provided with a radially protruding snap nose 40 that enters into a snap recess provided on the handle neck 4; cf. FIG. 10. In this way, an additional retention of the brush attachment 3 in the attached position is achieved.

When brush attachment 3 is removed again, the arresting piece 13 is moved in the opposite direction, back into its inner position. Here, an driving surface 27 provided on the coupling insert 9 drives the entraining surface 21 provided on the arresting piece 13, and thus the arresting piece 13, in the axial direction. Simultaneously, the snap hook 28 is unsnapped via a beveling on its snap nose 40; cf. FIG. 10. As the removal continues, the arresting piece 13 moves radially inward in the sliding block guide 34 so far that the inner contour of the brush attachment 3 can be pulled over the snap nose 18 of the arresting piece 13; cf. FIG. 11. Simultaneously, here the inner flat area 24 of the arresting piece 13 is seated on the flat area 31 of the drive shaft 5, which is thereby blocked.

Advantageously, the dirt receptacle depressions 41 are provided on the fit surfaces of the toothbrush handle and the attachment part, into which dust particles, dirt particles, and the like can, so to speak, slide, so that they do not hinder the coupling process. In particular, the ribbings 42 shaped as longitudinal channels can be provided on the outer surface of the arresting piece 13 and/or the outer surface of the handle neck 4 as the dirt receptacle depressions 42; cf. FIGS. 10 and 11.

An embodiment similar to FIGS. 10 and 11 is shown in FIGS. 12 and 13, according to which the arresting piece 13 is also designed as a slide block. As FIG. 12 shows, the arresting piece 13 is here also guided in a slide block guide 34 that converts an axial movement of the named arresting piece 13 into a transverse movement. Here, in the arresting piece 13, similar to the previously described embodiment, a slide block guide 35 is also provided that is designed in the form of a stepped longitudinal channel comprising the various guide segments 37, 38, and 39 having differing inclinations relative to the toothbrush longitudinal axis. In contrast to the embodiment according to FIGS. 10 and 11, however, the arresting piece 13 having the named guide slotted link 35 is guided only by one guide pin 36.

However, in order to prevent a tilting of the named arresting piece 13, the named arresting piece 13 has an abutting surface 26 that is oriented toward the attachment part 3 and that cooperates with an abutting surface 20 on a pressure piece 46 on the brush attachment 3. As FIGS. 12 and 13 show, in the interior of the connecting piece 7 of the brush attachment 3 a protruding pressure piece 46 is provided that, during the attaching of the brush attachment 3 onto the handle neck 4, enters into the named handle neck 4. The abutting surface 26 oriented toward handle 2 is seated on the abutting surface 20 of the arresting piece 13. As the brush attachment 3 is further attached, the named pressure piece 46 pushes the named arresting piece 13 back, such that the arresting piece is pressed outward away from the drive shaft 3 via a slide block guide 34, as is shown in FIG. 13.

Here, the named arresting piece 13 is loaded by a spring device 47 in the form of a pressure spring that pre-tensions the arresting piece 13 into its arresting position on the drive shaft 3, and that ensures that the named abutting surface pair 20 and 26 are situated tightly on one another during the pushing back by the pressure piece 46 of the brush attachment 3, causing the named arresting piece 13 to assume the desired orientation despite the presence of only one guide pin 36.

As shown in a comparison of FIGS. 12 and 13, the arresting piece 13 is lifted in this way off of the drive shaft 5 via the sliding block guide 34 during the attaching of the brush attachment 3, so that the drive shaft 5 is released. When the brush attachment 3 is removed again, the named spring device 47 forces the arresting piece 13 back into its arresting initial position, which is shown in FIG. 12 and in which the drive shaft 5 is blocked.

The depicted embodiment shown in FIGS. 14 and 15 corresponds in principle to the embodiment according to FIGS. 10 and 11, so that the same reference characters have been used for identical components, and to that extent reference is made to the preceding description. In the embodiment according to FIGS. 14 and 15 as well, the arresting piece 13 guided in the sliding block guide 34 is actuated via a snap element 43, designed as snap hook 44, on brush attachment 3, which protrudes towards the handle 2 in the interior of the connecting piece 7 of the brush attachment 3 and is matched in its position and shape to the named arresting piece 13 in such a way that it moves frontally against the named connecting piece 13 when the brush attachment 3 is attached onto the handle neck 4. The named snap element 43 is provided on its frontal end with an abutting surface 26 that moves against the abutting surface 20 of the arresting piece 13. In the manner shown in connection with FIGS. 10 and 11, this causes the arresting piece 13 to be pushed back and outward in the sliding block guide 34 when the brush attachment 3 is attached, so that on the one hand the drive shaft 5 is released and on the other hand the radially outward-protruding engagement part 11 of the arresting piece 13 locks the brush attachment 3 onto the handle neck 4, in that the named engagement part 11 moves into the window-type recess 25 in the connecting piece 7; cf. FIG. 15.

In addition, the brush attachment 3 is locked on the handle neck 4 by means of the snap element 43. As FIG. 15 shows, the named snap element 43, designed in the form of a radially movable spring clip, moves into the interior of the handle neck 4, such that the snap element 43 first slides with its protruding snap nose 40 over a contour situated on the inner jacket surface of the handle neck 4. When the brush attachment 3 has reached its fully attached position, the named snap element 43 is moved under spring force into an undercut of the named snap contour 48 of the handle neck 4, which causes the brush attachment 3 to be locked on the handle neck 4. As FIG. 15 shows, the snap surfaces that engage with one another on the snap nose 40 and the snap contour 48 are oriented essentially perpendicular to the direction of the attaching, so that a firm snapping in is ensured.

However, in order to enable a disengagement of the brush attachment 3 from the handle 2, at least one beveled surface 49 or 50 is provided on the named snap element 43 and/or on the arresting piece 13, so that during the removal of the attachment the arresting piece 13, which presses against the snap element, exerts a wedge effect on the snap hook 44 that causes the snap hook 44 to snap out of the snap contour 48 on the handle. The named arresting piece 13 is driven by the driving surface 21 and driving surface 27 that corresponds thereto on the recess 25, when the brush attachment 3 is removed from the handle 2.

The named arresting piece 13 can here be pre-tensioned in the previously described manner into its position in which it arrests the drive shaft 5 by a spring device that is not shown in more detail in FIG. 15. The snapping of the brush attachment 3 on the handle 2 compensates the pre-tension force of the spring device, so that this force does not cause an unwanted sliding of the brush attachment 3 off of the handle 2.

The depicted embodiment shown in FIG. 16 also provides, in a similar manner, a snap connection between the brush attachment 3 and the handle 2. To the extent that this embodiment agrees with the previously described embodiment according to FIGS. 14 and 15, reference is made to the description thereof, and the same reference characters have been provided. In contrast to the embodiment according to FIGS. 14 and 15, in the toothbrush according to FIG. 16, the snap element 43 comprising the snap hook 44 is provided in order to snap together with the handle neck 4 from the outer periphery. Here, the named snap hook 44 is designed in the form of a radially movable spring clip that extends on the inner periphery of the connecting piece 7 and essentially continues this periphery in a continuous manner, wherein the snap element 43 extends essentially parallel to the longitudinal axis of the connecting piece 7.

In particular, the named snap hook 44 can be provided on the coupling insert 9 in the interior of the connecting piece 7.

During the attaching of brush attachment 3, the named snap hook 44 at first slides over the outer contour of the handle neck 4, wherein the snap nose 40 causes the named snap hook 44 to expand elastically outward. When the fully attached position has been reached, the named snap hook 44 is snapped into an undercut snap contour 48 on the handle neck 4, which is designed there in the form of a recess or opening.

In order to enable the disengagement of the snap connection during the removal of the brush attachment 3, the snap nose 40 and/or snap contour 48 on the handle can be contoured in a suitable manner, for example in the form of a ball-shaped projection and a seat matched thereto. Alternatively, or in addition, similar to the above-described embodiment, a pair of oblique surfaces 49 and 50 can be provided on the snap hook 40 and on the arresting piece 13, exerting a wedge effect during the removal of the brush attachment 3 that on the one hand presses the arresting piece 13 radially inward and on the other hand presses the snap hook 44 radially outward.

FIG. 17 shows a further embodiment of a toothbrush 1 having an arresting piece 13 guided in a sliding block guide 34, wherein here as well, a snap element 43 in the form of a snap hook 44 is provided for the snap connection of the brush attachment 3 on the handle 2 of the toothbrush 1. Similar to the embodiment according to FIG. 16, the snap hook 44 is also provided on the inner periphery of the connecting piece 7, wherein the snap hook 44 extends essentially parallel to the longitudinal axis of the brush attachment 3. However, in contrast to the embodiment according to FIG. 16, the named snap hook 44 does not lock with the handle neck 4 itself, but rather with the arresting piece 13, when this arresting piece is in its outward-spread position in which it does not arrest the drive shaft 5; cf. FIG. 17. In the previously described manner, the arresting piece 13 simultaneously acts as a coupling piece that holds the brush attachment 3 on the handle neck 4, wherein the named arresting piece 13 moves with its radially outward-projecting engagement part 11 into the recess 25 in the connecting piece 7 of the brush attachment 3. Here, the named snap hook 44, which snaps together with a snap contour 48 that is undercut to this extent on the arresting piece 13, extends in the area of the named recess 25.

When the brush attachment 3 is attached the onto handle neck 4, on the one hand the arresting piece 13 is moved radially outward in the previously described manner via the sliding block guide 34. Here, at first the named snap hook 44 slides over the radially outwardly arranged back of the arresting piece 13, as soon as this arresting piece moves into the recess 25 on the brush attachment. When the completely attached position of brush attachment 3 has been reached, the snap hook 44 snaps back inward radially, so that the snap nose 40 falls into the snap contour 48, cooperating therewith, on the arresting piece 13. When brush attachment 3 is removed again, the named snap connection of the snap hook 44 ensures that the arresting piece 13 is moved back again. To this extent, the pair of snap surfaces on the snap nose 40 and the snap contour 48 can form the previously described driving surfaces 21 and 27 that drive the arresting piece 13 when the brush attachment 3 is removed again. In other respects, the embodiment according to FIG. 17 corresponds to the embodiment in the preceding Figures, so that to this extent reference is made to the description thereof, and the same reference characters are provided.

As FIG. 18 shows, in order to neutralize the pre-tension of the arresting piece 13 that can be applied by the previously described spring device, a pressure piece 46 can also be provided in the interior of the connecting piece 7 of the brush attachment 3, said pressure piece abuts frontally on the arresting piece 13; cf. FIG. 18. In the completely attached position of the brush attachment 3, the named arresting piece 13 is likewise snapped together with the snap hook 44 provided on the inner periphery of the connecting piece 7 or coupling insert 9, as is shown in FIG. 17.

FIG. 19 shows a further embodiment of the arresting means 23 for arresting or blocking the drive shaft 5. Similar to the previously described specific embodiments, here as well an axially movable arresting piece 13 is provided on the handle neck 4 that is displaceably mounted in a sliding guide in such a way that an axial movement of the arresting piece 13 simultaneously causes a transverse movement in the radial direction. As FIG. 19 shows, here the arresting piece 13 is displaceably guided in a channel guide that is fashioned as a dovetail channel guide in the depicted embodiment. The slotted link-type guide channels are here designed on the handle neck, wherein the arresting piece 13 advantageously is capable of running in the corresponding dovetail channels on opposite sides. Here, as FIG. 19 shows, the guide channels are inclined at an acute angle to the longitudinal direction of the handle 2, so that when the arresting piece 13 is pushed back toward the grip area, the arresting piece 13 is lifted off of the drive shaft 5. In the arresting position shown in FIG. 19, the named arresting piece 13 is seated in the previously described manner on a flat area of the drive shaft 5 in order to block said shaft.

Here, the arresting piece 13 is axially pre-tensioned into its arresting position by a spring device 47 in the form of a pressure spring. In order to disengage the locking of the drive shaft 5 during the attaching of the brush attachment 3, a frontally protruding ram having an abutting surface 26 is provided on the connecting piece 7 of the brush attachment 3, said surface moves against a likewise frontally situated abutting surface 20 on the arresting piece 13 in order to push the arresting piece back; cf. FIG. 19.

FIG. 20 shows an alternative embodiment of the arresting piece 13, according to which the arresting piece 13 can also be designed in the form of a pivotably mounted cam. In the depicted embodiment shown in FIG. 20, the arresting piece 13 is mounted, approximately in the area of the wall of the handle neck 4, so as to be pivotable about a transverse axis 51, so that the cam-type arresting piece 13 can be pivoted back and forth between an arresting position in which it stands in engagement with the drive shaft 5 and a non-arresting position in which it is not engaged with the named drive shaft 5.

The arresting piece 13 and its pivot bearing are here designed and arranged in such a way that in the arresting position, the engagement segment, which blocks the drive shaft 5, of the arresting piece 13 stands approximately perpendicular to the drive shaft 5; i.e., an imaginary line through the pivot axis of the arresting piece 13 and the point of engagement on the drive shaft 5 stands approximately perpendicular to the longitudinal axis of the drive shaft 5; cf. FIG. 20. Here, the arresting piece 13 is pre-tensioned into the named arresting position by a spring device 47 that can be designed as a pressure spring.

Similar to the previously described embodiments, here the arresting element 13 is automatically brought into its non-arresting position during the attaching of the brush attachment 3. For this purpose, a ram having an abutting surface 26 is provided on the connecting piece 7 of the brush attachment 3, said abutting surface presses against the cam-shaped arresting piece 13 during the pushing on (cf. FIG. 20), causing the arresting piece 13 to pivot back and thus to pivot away from the drive shaft 5, with deformation of the spring device 39.

When the brush attachment 3 is removed again, the named spring device 39 presses the arresting piece 13 back into its arresting position.

Of course, in this embodiment according to FIG. 20 a snap connection between the brush attachment 3 and the handle 2 can also be provided in the previously described manner FIGS. 21 and 22 show a further construction of the capability of a snap connection between the arresting piece 13 and the brush attachment 3. FIG. 21 shows an arresting piece 13 that corresponds essentially to the embodiment according to FIGS. 10 and 11, and that can be displaced in the manner already described via a sliding block guide 34. Here, a snap contour 53 is provided on the engagement part 11 of the arresting piece 13, which arresting piece can be moved into the previously described window-type recess 25 of the brush attachment 3 in order to lock the brush attachment on the handle neck, said snap contour is undercut in the radial direction relative to the longitudinal axis of the toothbrush. Concretely, in the depicted embodiment two snap depressions arranged on opposite sides of the arresting piece 13 are provided which are designed in the manner of well-shaped depressions.

By means of these snap contours on opposite sides, the arresting piece 13 can be locked when it is moved back into its position on the brush attachment 3 in which it releases the drive shaft 5. For this purpose, the brush attachment has, in the area of the named window-type recess 25, two snap contours arranged opposite one another and also undercut in the radial direction, in the form of snap projections 54; cf. FIG. 22. The named snap contours 54 are here designed so as to be resilient so that they can move apart from one another when the arresting piece 13 enters between the named snap projections 54. In this way, the named snap projections 54 can slide over the sides of the arresting piece 13 until they are able to fall into the snap depressions 53 provided there.

The brush attachment can be held securely on the handle neck 4 by means of this snap connection via the snap contours 53 and 54. In addition, the spring pre-tension of the arresting piece 13 can also be neutralized, because the snap connection of the arresting piece 13 holds the arresting piece in its, so to speak, extended position.

Alternatively, or in addition, the snap connection of the named arresting piece 13 can also take place at the handle neck 4. In this case, the snap projections 54, shown in FIG. 22 and arranged opposite one another, are not provided on the connecting piece 7 of the brush attachment 3, but rather are provided on the handle neck 4. In this construction as well, the arresting piece 13 is snapped into its extended position in which it releases the drive shaft 5, so that the spring pre-tension can be neutralized. Nonetheless, optionally a locking of the brush attachment 3 on the handle neck 4 can also be achieved here, because the engagement part 11 of the arresting piece 13 can in this case enter or protrude, so to speak, through a window in the handle neck 4 and also through a window in the brush attachment 3.

What is claimed is:

1. A toothbrush handle of an electric toothbrush that is capable of use with an attachment part, the handle including a housing; a neck; a coupling device located in the handle neck for coupling an attachment part thereto; a drive mechanism for driving an attachment part coupled to the coupling device; and mechanical arresting means for preventing operation of the drive mechanism, wherein when an attachment part is coupled to the coupling device the arresting means are released; and further wherein when an attachment part is removed from the coupling device the arresting means are activated; wherein the arresting means has a movably mounted arresting piece for engagement with the drive mechanism such that at least one rod is pivotably linked at one end to the handle neck and is pivotably linked at its other end to the arresting piece.

2. The toothbrush handle according to claim 1, further comprising an electronic switch-off device, wherein the switch-off device switches off the drive mechanism when the arresting means are activated.

3. The toothbrush handle according to claim 2, wherein the switch-off device has detecting means for detecting the motor current, and has switch-off means for switching off the drive motor when a predetermined motor current has been exceeded.

4. The toothbrush handle according to claim 1, wherein the arresting piece is axially moveable in the longitudinal direction of the handle.

5. The toothbrush handle according to claim 1, wherein the at least one rod is a parallelogram rod guide that has at least two rods that are oriented approximately parallel to one another.

6. The toothbrush handle according to claim 1, wherein a spring device is allocated to the arresting piece in order to pre-tension the arresting piece into its activated position.

7. An electric toothbrush having a toothbrush handle according to claim 1.

8. A toothbrush handle of an electric toothbrush that is capable of use with an attachment part, the handle including a housing; a neck; a coupling device located in the handle neck for coupling an attachment part thereto; a drive mechanism for driving an attachment part coupled to the coupling device; and mechanical arresting means for preventing operation of the drive mechanism, wherein when an attachment part is coupled to the coupling device the arresting means are released; and further wherein when an attachment part is removed from the coupling device the arresting means are activated; wherein the arresting means has a movably mounted arresting piece for engagement with the drive mechanism, wherein the arresting piece is designed as a pivotably mounted cam.

9. A toothbrush handle of an electric toothbrush that is capable of use with an attachment part, the handle including a housing; a neck; a coupling device located in the handle neck for coupling an attachment part thereto; a drive mechanism for driving an attachment part coupled to the coupling device; and mechanical arresting means for preventing operation of the drive mechanism, wherein when an attachment part is coupled to the coupling device the arresting means are released; and further wherein when an attachment part is removed from the coupling device the arresting means are activated; wherein the arresting means has a movably mounted arresting piece for engagement with the drive mechanism, wherein the arresting piece has a catch segment that is matched in its shape and position to a counterpiece on the attachment part, for catching the counterpiece on the attachment part during the attaching of the attachment part onto the handle neck, and for the axial displacement of the arresting piece into its disengaged position.

* * * * *